(12) United States Patent
Dar et al.

(10) Patent No.: US 9,095,417 B2
(45) Date of Patent: Aug. 4, 2015

(54) ADJUSTABLE ORTHOSIS FOR ELECTRICAL STIMULATION OF A LIMB

(75) Inventors: Amit Dar, Kfar Hess (IL); Shmuel Springer, Modi'in (IL); Eyal Lasko, Tel Mond (IL); Jonathan Bar-Or, Pardes Hanna (IL)

(73) Assignee: Bioness Neuromodulation Ltd., Raanana (IL)

( * ) Notice: Subject to any disclaimer, the term of this patent is extended or adjusted under 35 U.S.C. 154(b) by 667 days.

(21) Appl. No.: 13/022,149

(22) Filed: Feb. 7, 2011

(65) Prior Publication Data

US 2012/0203156 A1    Aug. 9, 2012

(51) Int. Cl.
*A61F 5/00* (2006.01)
*A61F 5/01* (2006.01)
*A61N 1/04* (2006.01)
*A61N 1/36* (2006.01)

(52) U.S. Cl.
CPC .............. *A61F 5/01* (2013.01); *A61F 5/0106* (2013.01); *A61F 5/0111* (2013.01); *A61F 5/0118* (2013.01); *A61N 1/0452* (2013.01); *A61N 1/0484* (2013.01); *A61N 1/36003* (2013.01)

(58) Field of Classification Search
CPC ....... A61F 5/01; A61F 5/0106; A61F 5/0111; A61F 5/0118; A61N 1/0452; A61N 1/0484; A61N 1/36003
USPC ................ 602/16, 20–28; 128/878–879, 882; 482/127, 136
See application file for complete search history.

(56) References Cited

U.S. PATENT DOCUMENTS

| | | | |
|---|---|---|---|
| 1,422,396 A | 7/1922 | Wappler |
| 1,644,803 A | 10/1927 | Wappler |
| 3,204,637 A | 9/1965 | Frank et al. |
| 3,344,792 A | 10/1967 | Offner et al. |
| 3,881,496 A | 5/1975 | Vredenbregt et al. |
| 4,381,012 A | 4/1983 | Russek |

(Continued)

FOREIGN PATENT DOCUMENTS

| | | |
|---|---|---|
| JP | 1985-119949 A | 6/1985 |
| JP | 2004-313555 A | 11/2004 |

(Continued)

OTHER PUBLICATIONS

Examination Report for Australian Application No. 2006314072, mailed on May 5, 2010, 4 pages.

(Continued)

*Primary Examiner* — Michael Brown
(74) *Attorney, Agent, or Firm* — Cooley LLP

(57) ABSTRACT

Systems, devices and methods for treating a targeted body tissue (e.g., bone, soft tissue, muscle, ligaments, etc.) by stimulating the body tissue with an electric current are described herein. In one embodiment, an apparatus includes a first orthosis member that includes a first electrode. The first orthosis member is configured to be disposed about a first portion of a limb of a user of the apparatus such that the first electrode is in contact with the first portion of the limb. The apparatus includes a second orthosis member that includes a second electrode. The second orthosis member is configured to be disposed about a second portion of the limb such that the second electrode is in contact with the second portion of the limb. A connector is configured to couple the second orthosis member to the first orthosis member and the connector has a selectively adjustable length.

27 Claims, 22 Drawing Sheets

(56) References Cited

U.S. PATENT DOCUMENTS

| | | | |
|---|---|---|---|
| 4,432,368 A | 2/1984 | Russek | |
| 4,558,704 A | 12/1985 | Petrofsky | |
| 4,580,569 A | 4/1986 | Petrofsky | |
| 4,586,495 A * | 5/1986 | Petrofsky | 602/2 |
| 4,697,808 A | 10/1987 | Larson et al. | |
| 4,745,930 A | 5/1988 | Confer | |
| 4,982,732 A | 1/1991 | Morris | |
| 5,112,296 A | 5/1992 | Beard et al. | |
| 5,116,296 A | 5/1992 | Watkins et al. | |
| 5,121,747 A | 6/1992 | Andrews | |
| 5,277,697 A | 1/1994 | France et al. | |
| 5,330,516 A | 7/1994 | Nathan | |
| 5,403,002 A * | 4/1995 | Brunty | 473/438 |
| 5,437,619 A * | 8/1995 | Malewicz et al. | 602/20 |
| 5,476,441 A | 12/1995 | Durfee et al. | |
| 5,487,759 A | 1/1996 | Bastyr et al. | |
| 5,540,735 A | 7/1996 | Wingrove | |
| 5,562,707 A | 10/1996 | Prochazka et al. | |
| 5,628,722 A | 5/1997 | Solomonow et al. | |
| 5,643,332 A | 7/1997 | Stein | |
| 5,724,996 A * | 3/1998 | Piunti | 128/898 |
| 5,748,845 A | 5/1998 | Labun et al. | |
| 5,814,093 A | 9/1998 | Stein | |
| 5,851,191 A | 12/1998 | Gozani | |
| 5,861,017 A | 1/1999 | Smith et al. | |
| 5,916,159 A | 6/1999 | Kelly et al. | |
| 5,951,598 A | 9/1999 | Bishay et al. | |
| 5,983,140 A | 11/1999 | Smith et al. | |
| 6,002,965 A | 12/1999 | Katz et al. | |
| 6,019,877 A | 2/2000 | Dupelle et al. | |
| 6,064,912 A * | 5/2000 | Kenney | 607/48 |
| 6,129,695 A | 10/2000 | Peters et al. | |
| 6,179,799 B1 | 1/2001 | Doran | |
| 6,282,448 B1 | 8/2001 | Katz et al. | |
| 6,308,102 B1 | 10/2001 | Sieracki et al. | |
| 6,438,428 B1 | 8/2002 | Axelgaard et al. | |
| 6,445,955 B1 | 9/2002 | Michelson et al. | |
| 6,456,884 B1 | 9/2002 | Kenney | |
| 6,456,885 B1 | 9/2002 | Shiba et al. | |
| 6,496,739 B2 | 12/2002 | Arbel | |
| 6,567,706 B2 | 5/2003 | Bar-Or et al. | |
| 6,571,115 B2 | 5/2003 | Axelgaard et al. | |
| 6,607,500 B2 | 8/2003 | Da Silva et al. | |
| 6,618,624 B2 | 9/2003 | Elias | |
| 6,692,453 B2 | 2/2004 | Wolfe | |
| 6,829,510 B2 | 12/2004 | Nathan et al. | |
| 7,011,637 B2 | 3/2006 | Sherman et al. | |
| 7,146,220 B2 | 12/2006 | Dar et al. | |
| 7,158,822 B2 | 1/2007 | Payne, Jr. | |
| 7,162,305 B2 | 1/2007 | Tong et al. | |
| 7,337,007 B2 * | 2/2008 | Nathan et al. | 607/48 |
| 7,403,821 B2 | 7/2008 | Haugland et al. | |
| 7,410,471 B1 | 8/2008 | Campbell et al. | |
| 7,416,537 B1 | 8/2008 | Stark et al. | |
| 7,537,573 B2 | 5/2009 | Horst | |
| 7,756,585 B2 | 7/2010 | Embrey et al. | |
| 7,785,279 B2 | 8/2010 | Sankai | |
| 7,899,556 B2 | 3/2011 | Nathan et al. | |
| 8,070,703 B2 * | 12/2011 | Skahan et al. | 602/23 |
| 8,209,022 B2 | 6/2012 | Dar et al. | |
| 8,209,036 B2 | 6/2012 | Nathan et al. | |
| 8,382,688 B2 | 2/2013 | Dar et al. | |
| 8,694,110 B2 | 4/2014 | Nathan et al. | |
| 8,868,217 B2 | 10/2014 | Dar et al. | |
| 2001/0039444 A1 | 11/2001 | Bar-Or et al. | |
| 2002/0077688 A1 | 6/2002 | Kirkland | |
| 2003/0040788 A1 | 2/2003 | Dupelle et al. | |
| 2003/0050673 A1 | 3/2003 | Yamakazi et al. | |
| 2003/0065368 A1 | 4/2003 | Van Der Hoeven | |
| 2003/0083596 A1 | 5/2003 | Kramer et al. | |
| 2003/0114894 A1 | 6/2003 | Dar et al. | |
| 2004/0082979 A1 | 4/2004 | Tong et al. | |
| 2004/0122483 A1 | 6/2004 | Nathan et al. | |
| 2004/0172097 A1 | 9/2004 | Brodard et al. | |
| 2004/0173220 A1 | 9/2004 | Harry et al. | |
| 2004/0243197 A1 | 12/2004 | Demian | |
| 2004/0254624 A1 | 12/2004 | Johnson | |
| 2005/0043660 A1 | 2/2005 | Stark et al. | |
| 2005/0131317 A1 | 6/2005 | Oddsson et al. | |
| 2006/0211956 A1 | 9/2006 | Sankai | |
| 2007/0106343 A1 | 5/2007 | Monogue et al. | |
| 2007/0112394 A1 | 5/2007 | Nathan et al. | |
| 2007/0179560 A1 | 8/2007 | Tong et al. | |
| 2007/0197946 A1 | 8/2007 | Gilmour | |
| 2007/0203533 A1 | 8/2007 | Goren et al. | |
| 2008/0045872 A1 | 2/2008 | Bauerfeind et al. | |
| 2008/0154113 A1 | 6/2008 | Zilberman | |
| 2008/0294080 A1 | 11/2008 | Adarraga | |
| 2009/0012436 A1 | 1/2009 | Lanfermann et al. | |
| 2009/0177131 A1 | 7/2009 | Dar et al. | |
| 2011/0137375 A1 | 6/2011 | McBride | |
| 2012/0330375 A1 | 12/2012 | Nathan et al. | |
| 2012/0330394 A1 | 12/2012 | Dar et al. | |
| 2012/0330395 A1 | 12/2012 | Dar et al. | |

FOREIGN PATENT DOCUMENTS

| | | |
|---|---|---|
| WO | WO 02/074109 A2 | 9/2002 |
| WO | WO 2004/098703 | 11/2004 |

OTHER PUBLICATIONS

Examination Report for Australian Application No. 2006314072, mailed on Jul. 5, 2011, 2 pages.

Office Action for Canadian Application No. 2,632,196, mailed on Mar. 16, 2010, 4 pages.

Office Action for U.S. Appl. No. 12/096,077, mailed Apr. 5, 2012, 10 pages.

Office Action for U.S. Appl. No. 13/036,256, mailed Apr. 5, 2012, 8 pages.

International Search Report and Written Opinion for International Application No. PCT/IL2012/000260, mailed Oct. 9, 2012, 13 pages.

International Search Report and Written Opinion for International Application No. PCT/IL2012/000063, mailed Jun. 29, 2012, 11 pages.

Office Action for U.S. Appl. No. 13/532,597, mailed Apr. 23, 2013.

Office Action for U.S. Appl. No. 13/169,553, mailed Apr. 29, 2013.

Office Action for U.S. Appl. No. 13/169,553, mailed Sep. 17, 2013.

Alon, G. et al., "Persons with C5 or C6 tetraplegia achieve selected functional gains using a neuroprosthesis," Arch. Phys. Med. Rehabil., 84:119-124 (Jan. 2003).

Daly, W. K., "Electrodes installed in roll-on suspension sleeves," From "MEC '02 The Next Generation," Proceedings of the 2002 MyoElectric Controls/Powered Prosthetics Symposium Fredericton, New Brunswick, Canada: Aug. 21-23, 2002, University of New Brunswick.

Duncan, R. M., "Basic principles of splinting the hand," Journal of the American Physical Therapy Association, 69(12):1104-1116 (1989).

Hart, R. L. et al., "A comparison between control methods for implanted FES hand-grasp systems," IEEE Transactions on Rehabilitation Engineering, 6(2):208-218 (Jun. 1998).

Hendricks, H. T. et al., "Functional electrical stimulation by means of the 'Ness Handmaster Orthosis' in chronic stroke patients: an exploratory study," Clinical Rehabilitation, 15:217-220 (2001).

Popovic, M. R. et al., "Neuroprostheses for grasping," Neurological Research, 24:443-452 (2002).

Popovic, M. R. et al., "Neuroprostheses for grasping," Neurological Research, 24:443-452 (Jul. 2002).

Prochazka, A. et al., "The bionic glove: An electrical stimulator garment that provides controlled grasp and hand opening in quadriplegia," Arch. Phys. Med. Rehabil., 78:608-614 (Jun. 1997).

Stanic, U., "History of functional electrical stimulation," International Functional Electrical Stimulation Society, INS & IFESS Joint Congress, Sep. 16-20, 1998, Lucerne, Switzerland.

Strojnik, P. et al., "Implantable stimulators for neuromuscular control," Chapter 78 in The Biomedical Engineering Handbook: Second Edition, Bronzino, J. D. (ed.), Boca Raton: CRC Press LLC (2000).

(56) References Cited

OTHER PUBLICATIONS

Uellendahl, J. E. et al., "Custom silicone sockets for myoelectric prostheses," Journal of Prosthetics and Orthotics, 18(2):35-40 (2006).

Uellendahl, J. E. et al., "Custom silicone sockets for myoelectric prostheses," From "MEC '05 Intergrating Prosthetics and Medicine," Proceedings of the 2005 MyoElectric Controls/Powered Prosthetics Symposium, held in Fredericton, New Brunswick, Canada, Aug. 17-19, 2005, 6 pages.

Vodovnik, L. et al., "Functional electrical stimulation for control of locomotor systems," CRC Critical Reviews in Bioengineering, 6(2):63-131 (Sep. 1981).

Ward, A. R. et al., "Russian electrical stimulation: The early experiments," Physical Therapy, 82(10):1019-1030 (Oct. 2002).

Supplementary European Search Report for European Application No. 12745088.0, mailed Jun. 6, 2014.

"Clinical evaluation of the ljubljana functional electrical peroneal brace," Subcommittee on Evaluation, Committee on Prosthetics Research and Development Division of Medical Sciences—National Research Council, National Academy of Sciences, Washington, D.C., Report E-7 (1973).

Davis, R. et al., "Evaluation of electrical stimulation as a treatment for the reduction of spasticity," Bulletin of Prosthetics Research, Department of Medicine and Surgery Veterans Administration, Washington, D.C., pp. 302-309 (1974).

Kralj, A. et al., "Functional electrical stimulation of the extremities: part 1," Journal of Medical Engineering and Technology, pp. 12-15 (Jan. 1977).

Kralj, A. et al., "Functional electrical stimulation of the extremities: part 2," Journal of Medical Engineering and Technology, pp. 75-80 (Mar. 1977).

Liberson, W. T. et al., "Functional Electrotherapy: Stimulation of the Peroneal Nerve Synchronized with the Swing Phase of the Gait of Hemiplegic Patients," Archives of Physical Medicine & Rehabilitation, pp. 101-105 (Feb. 1961).

Popovic, M. R. et al., "Functional electrical therapy: retraining grasping in spinal cord injury," Spinal Cord, 44:143-151 (2006).

Stopar, M. et al., "New stimulators for cutaneous stimulation," Advances in External Control of Human Extremities, Proceedings of the Seventh International Symposium on External Control of Human Extremities, pp. 267-272 (1981).

Waters, R. L. et al., "Effectiveness of selected surface electrodes for motor stimulation," Advances in External Control of Human Extremities, Proceedings of the Sixth International Symposium on External Control of Human Extremities, pp. 31-38 (1978).

Waters, R. et al., "Treatment of the hemiplegic upper extremity using electrical stimulation and biofeedback training," Report to the Veterans Administration, Contract V600P-1064-79, Funding Period Sep. 27, 1979-Sep. 30, 1980, pp. 251-266.

\* cited by examiner

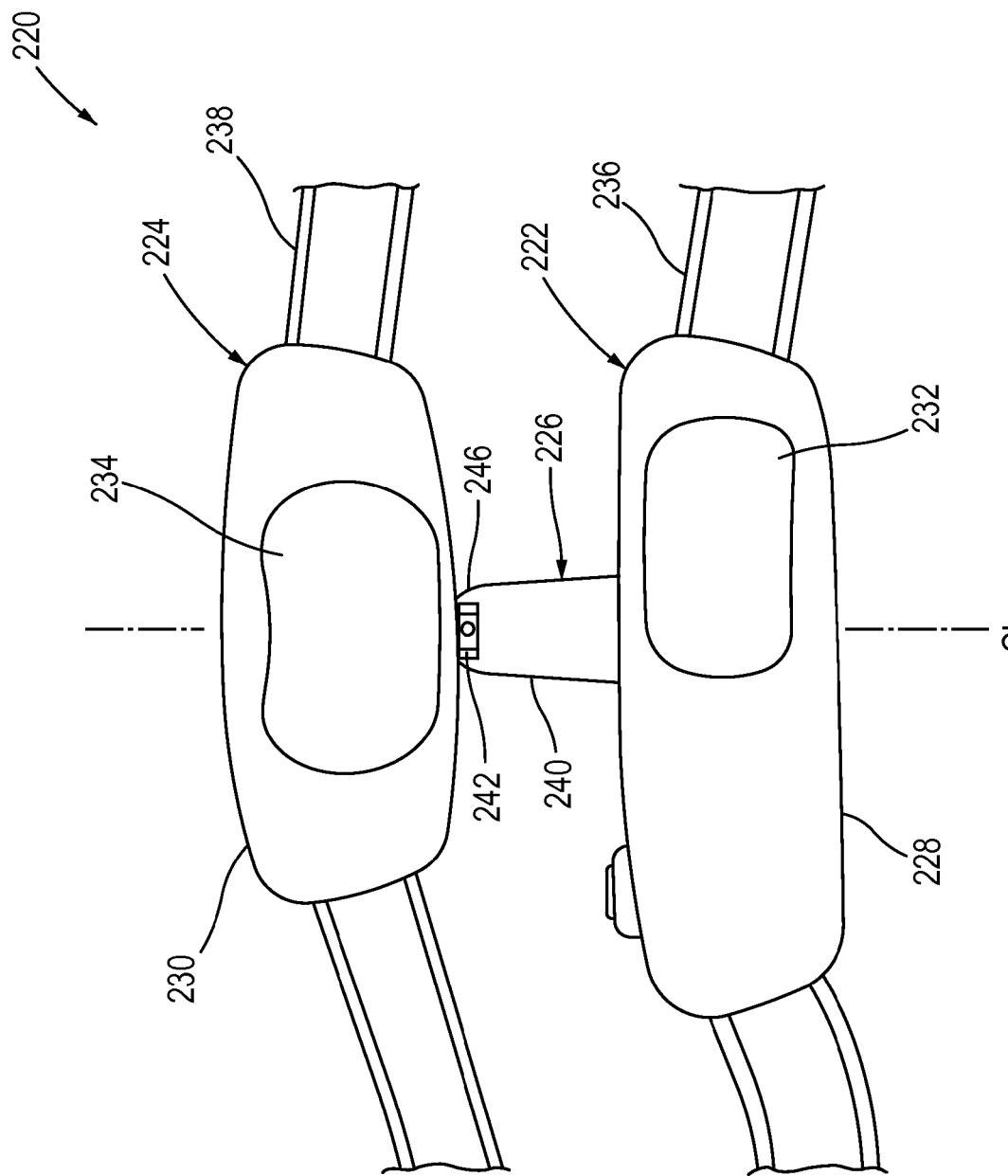

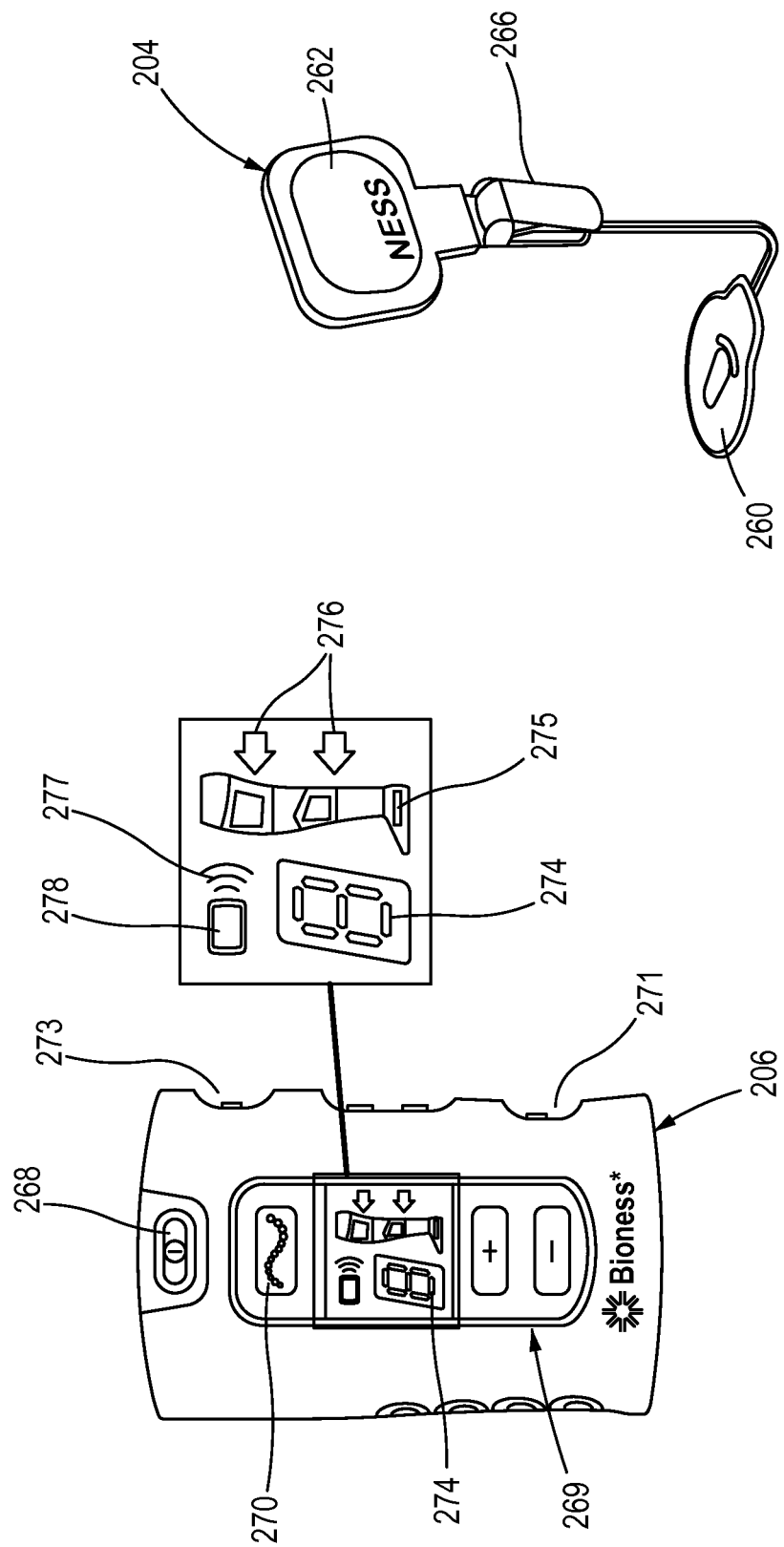

ADJUSTABLE ORTHOSIS FOR ELECTRICAL STIMULATION OF A LIMB

BACKGROUND

The invention relates generally to medical devices and more particularly to a surface neuroprosthesis device and method for functional electrical stimulation of a limb.

A surface neuroprosthesis device, also referred to as an orthosis device, such as a splint, cuff or garment, can be used in conjunction with an electrode to provide electrical stimulation of, for example, paralyzed limbs in therapeutic exercises and for generating limb function during functional electrical stimulation (FES).

FES is a means to communicate with the neuromuscular system for producing contraction in muscles or sensory input to the body. FES can be used in neuroprostheses for restoring active function to, for example, paralyzed or plegic body limbs in patients suffering disease or trauma to the central nervous system, in neurological conditions such as stroke, spinal cord injury, head injury, cerebral palsy and multiple sclerosis. Surface FES systems use controlled electrical currents through electrodes placed on the surface of the body, to trigger contraction from muscles underlying the electrode or to input sensory stimulus. Surface neuroprostheses can coordinate the FES-activation of several muscles of the limb alone, or in coordination with voluntary activation of muscles under natural neurological control.

Surface neuroprostheses are used for functional activities such as walking, standing, gripping/releasing objects, etc. Known devices for use in surface electrical stimulation that have been developed for activating specific body sites include, for example, dropfoot systems, which activate the ankle joint, modifying hemiplegic gait; hybrid FES-orthosis systems for restoring gait in spinal cord-injured patients, and systems for therapeutic activation and functional restoration of the hand.

Some neuroprosthesis devices based on FES have been developed for activating specific sites of the body by stimulating the muscles to contract and relax. Such devices for the lower limb include gait modification systems, such as a dropfoot system that can activate the ankle joint to prompt dorsiflexion, and systems that can activate the knee joint. Some neuroprosthesis devices based on FES are used to stimulate other limbs, such as arms.

In many of the known FES devices, the neuroprosthesis device is limited for use at a single location on the patient's body to provide electrical stimulation to a particular nerve, muscle or muscle group. In addition, many known FES devices have a preset size (e.g., length and/or circumferential dimension) to fit a patient's limb.

Thus, there is a need for a neuroprosthesis device configured for use in the electrical stimulation of more than one nerve, muscle or muscle group and that can be easily moved by a patient to different desired treatment locations. There is also a need for a neuroprosthesis device for use in the electrical stimulation of a nerve, muscle or muscle group that can be adjusted to accommodate different types of limbs (e.g., arms, legs, etc.) and patients having different sized limbs.

SUMMARY OF THE INVENTION

Systems, devices and methods for treating a targeted body tissue (e.g., muscles, bones, soft tissue, nerves, ligaments, etc.) by stimulating the body tissue with an electric current are described herein. In one embodiment, an apparatus includes a first orthosis member that includes a first electrode. The first orthosis member is configured to be disposed about a first portion of a limb of a user of the apparatus such that the first electrode is in contact with the first portion of the limb. The apparatus includes a second orthosis member that includes a second electrode. The second orthosis member is configured to be disposed about a second portion of the limb such that the second electrode is in contact with the second portion of the limb. A connector is configured to couple the second orthosis member to the first orthosis member and the connector has a selectively adjustable length such that a distance between the first orthosis member and the second orthosis member is selectively varied.

BRIEF DESCRIPTION OF THE DRAWINGS

FIG. 4B is a back view of a portion of the orthosis device of FIG. 2 shown with an electrode positioned at a second location on the orthosis device.

FIG. 12 is a front view of a control unit according to an embodiment.

FIG. 13 is a perspective view of a gait sensor according to an embodiment.

DETAILED DESCRIPTION

Figure 1:
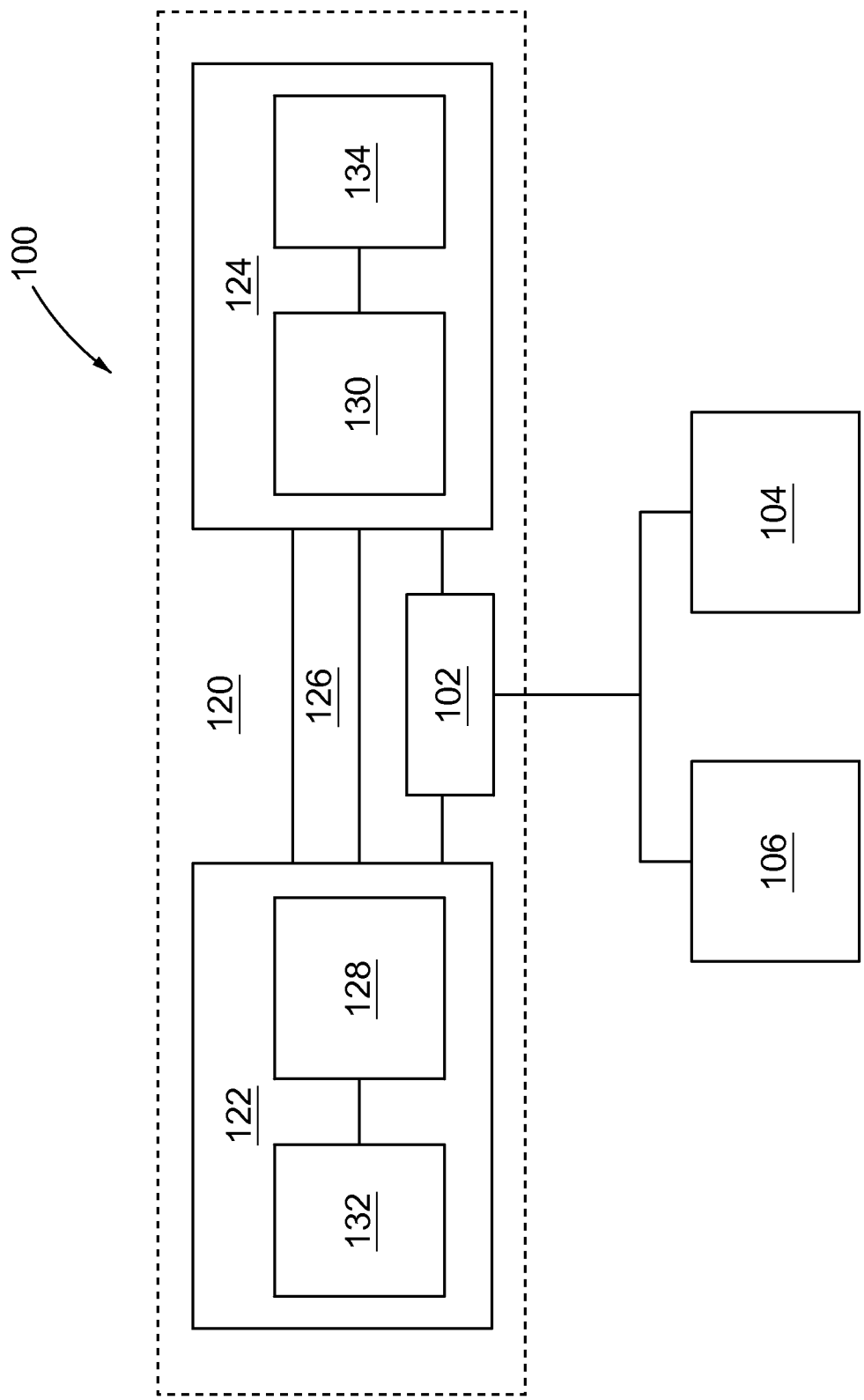
FIG. 1 is a schematic illustration of an orthosis system according to an embodiment.

Devices, systems and methods are described herein that can include one or more neuroprosthesis devices that can be used for functional electrical stimulation of a targeted body tissue (e.g., nerve(s), muscle(s)), such as in connection with an impaired limb. For example, in some embodiments, such treatment includes the functional electrical stimulation of intact nerves of limbs to trigger a muscle contraction or response. A surface neuroprosthesis device or orthosis device, can be for example, a cast, splint, cuff, wristlet, gauntlet, strap, sock, sleeve, thigh cover or other garment that can be worn by a patient (also referred to herein as "user") and that includes one or more electrodes that can be in contact with the skin of the patient.

Central nervous system (CNS) injuries often cause a gait disorder called foot drop. In addition, many patients with CNS injuries also suffer from thigh muscle weakness as well as foot drop. People who have foot drop are unable to raise their foot while walking and often drag their foot resulting in instability and increased effort during gait. Weakness of the muscles of the upper portion of the leg (i.e., quadriceps and hamstring) is associated with considerable difficulties with flexing or extending the knee during ambulation. In some embodiments, the devices and systems described herein can provide ankle dorsiflexion and knee flexion or extension in people suffering from foot drop and/or thigh muscle weakness following an upper motor neuron injury or disease (e.g., stroke, traumatic brain injury, multiple sclerosis, cerebral palsy, or incomplete spinal cord injury). In some embodiments, devices and systems described herein can be used to help hip movement (e.g., flexion, extension, adduction, abduction, internal rotation and/or external rotation). In some embodiments, devices and systems described herein can be used to help with movement of, for example, a thumb and fingers, wrist, a forearm, elbow, arm, and/or shoulder.

In some embodiments, the devices and systems described herein can be configured to communicate wirelessly to send electrical pulses to the nerves that contract the muscles of the lower leg and thigh. The stimulation of the muscles causes contraction of the muscles, which in turn can raise the foot and extend or flex the knee, which can in some instances, help improve gait, facilitate muscle re-education, prevent or retard disuse atrophy, maintain or increase joint range of motion and/or increase local blood flow.

As described herein, in some embodiments, an orthosis device can be used for the electrical stimulation treatment of multiple different limbs having different sizes and can accommodate a limb that changes shape when the muscles contract and release. An orthosis device as described herein can include an adjustable connector coupled to a first orthosis member and a second orthosis member. The first and second orthosis members can each include one or more electrodes configured to contact a patient's skin and provide electrical stimulation to a muscle. The connector can allow for adjustability of a longitudinal length of the orthosis device to accommodate use on patients having various sized limbs. The orthosis members can be coupled to the connector such that the orthosis members have freedom of motion and maintain good contact (i.e., contact sufficient to provide electrical stimulation to the relevant tissue) between the electrode(s) and the patient's skin while the limb is in motion and the muscles change shape.

In some embodiments, an apparatus includes a first orthosis member that includes a first electrode. The first orthosis member is configured to be disposed about a first portion of a limb of a user of the apparatus such that the first electrode is in contact with the first portion of the limb. The apparatus includes a second orthosis member that includes a second electrode. The second orthosis member is configured to be disposed about a second portion of the limb such that the second electrode is in contact with the second portion of the limb. A connector is configured to couple the second orthosis member to the first orthosis member and the connector has a selectively adjustable length.

In some embodiments, an apparatus includes an orthosis including a first cuff member and a second cuff member. The second cuff member is configured to be coupled to the first cuff member at a preselected distance from the first cuff member. The first cuff member is configured to have a first electrode (or array of electrodes) coupled thereto and the second cuff member is configured to have a second electrode coupled thereto. The orthosis is configured to be disposed in a first position on a limb of a user such that a visual locator disposed on the orthosis is positioned at a first location on an outer portion of the limb, the first cuff member is disposed about the limb such that the first electrode is in contact with a first portion of the limb, and the second cuff member is disposed about the limb such that the second electrode (or array of electrodes) is in contact with a second portion of the limb. The orthosis is configured to be disposed in a second position on the limb such that the visual locator is positioned at a second location on the outer portion of the limb, the first cuff member is disposed about the limb such that the first electrode is in contact with a third portion of the limb, and the second cuff member is disposed about the limb such that the second electrode is in contact with a fourth portion of the limb.

In some embodiments, an apparatus includes a first orthosis member including a first electrode. The first orthosis member is configured to be disposed about a first portion of a thigh of a user of the apparatus such that the first electrode is in contact with the first portion of the thigh. The apparatus includes a second orthosis member including a second electrode. The second orthosis member is configured to be disposed about a second portion of the thigh of the user such that the second electrode is in contact with the second portion of the thigh. The first portion of the thigh is at a first distance from a knee of the user and the second portion of the thigh is at a second distance from the knee of the user. The second distance is greater than the first distance. A connector is configured to couple the second orthosis member to the first orthosis member. The connector includes a first connector member coupled to the first orthosis member and a second connector member coupled to the second orthosis member. The first connector member is couplable to the second connector member such that the connector has a preselected length between the first orthosis member and the second orthosis member.

As used in this specification, the singular forms "a," "an" and "the" include plural referents unless the context clearly dictates otherwise. Thus, for example, the term "an electrode" is intended to mean a single electrode or a combination of electrodes.

FIG. 1 is a schematic illustration of an embodiment of an orthosis system that can be used for the functional electrical stimulation of a target body tissue (e.g., nerve, muscle, ligaments, etc.). An orthosis system 100 can include an orthosis device 120 (also referred to as a "neuroprosthesis device"), a gait sensor 104 and a control unit 106. The orthosis device 120 includes a first orthosis member 122, a second orthosis member 124, a connector 126 and a stimulator unit 102.

The first orthosis member 122 includes a first panel or cuff 128 and one or more electrodes 132 removably couplable to the first panel 128. The second orthosis member 124 includes a second panel or cuff 130 and one or more electrodes 134 removably couplable to the second panel 130. The first orthosis member 122 and the second orthosis member 124 are each configured to be coupled to a limb of a patient such that the one or more electrodes 132 and 134 contact the skin of the patient. For example, the first orthosis member 122 and the second orthosis member 124 can each be coupled to an arm or a leg of the patient. In some embodiments, the first orthosis member 122 and the second orthosis member 124 can each include an adjustable strap or straps to secure the orthosis member to the limb of the patient. The strap(s) can include a coupling mechanism to releasably couple a first strap member to a second strap member. In some embodiments, the coupling mechanism includes a magnetic attachment.

The electrode(s) 132 and 134 can each be coupled to an interior surface of the panels 128 and 130, respectively, with for example, VELCRO patches, press-studs, snaps, magnets, or specialized holders that press a conductive back of the electrode(s) 132 and 134 against a conductive stud or panel inside the orthosis members 122 and 124, or a combination thereof. The electrode(s) 132 and 134 can each make electrical contact with the skin and can include a conductive pad assembly that is held onto a part of the body with the orthosis members 122 and 124. In some embodiments, the electrode(s) 132 and/or the electrode(s) 134 can be hydrogel electrodes. In some embodiments, the electrode(s) 132 and/or the electrode(s) 134 can be a cloth electrode. For example, in some embodiments, the electrode(s) 132 and/or electrode(s) 134 can include a metal mesh conductor and an absorbent pad, all of which can be soaked in water. For example, the electrode(s) 132 and/or the electrode(s) 134 can include a pad formed with an absorptive material, such as felt, cloth, velvet, viscose, etc., such that the pad can be saturated with liquid (e.g., water) prior to use. In some embodiments, the electrode(s) 132 and/or the electrode(s) 134 can include a base portion that can be attached to an interior surface of an orthosis and an electrode assembly including an electrode element and a pad that contacts the surface of the patient's skin. The electrode(s) 132 and the electrode(s) 134 can be removably coupled to the first panel 128 and the second panel 130, respectively, such that the electrode(s) 132 and 134 can be easily removed and replaced as needed. The electrode(s) 132 and 134 can be, for example, disposable.

In some embodiments, an electrode(s) 132 can be selectively positioned on the first panel 128 and/or an electrode(s) 134 can be selectively positioned on the second panel 130. For example, the first panel 128 and/or the second panel 130 can include a marking ring indicating where an electrode 132 or 134 is to be positioned for a particular treatment and/or a particular patient. In some embodiments, one or more electrodes 132 and/or 134 can be positioned centered on the first panel 128 and/or the second panel 130. In some embodiments, one or more electrodes 132 and/or 134 can be positioned off-center on the first panel 128 and/or the second panel 130.

The connector 126 can couple the first panel 128 to the second panel 130. In some embodiments, the connector 126 can limit movement of the second panel 130 relative to the first panel 128 along a longitudinal axis of the limb on which the orthosis device 120 is coupled. In some embodiments, the connector 126 can limit movement of the second panel 130 relative to the first panel 128 in a direction along a longitudinal axis of the connector 126. The connector 126 can be adjustable along the longitudinal axis of the connector 126. For example, the connector 126 can be selectively adjusted to vary the distance between the first panel 128 and the second panel 130. In this manner, the orthosis device 120 can be adjusted to fit a particular patient. Thus, a distance between an electrode 132 on the first panel 128 and an electrode 134 on the second panel 130 can also be selectively adjusted.

In some embodiments, the connector 126 can include a first connector member (not shown in FIG. 1) and a second connector member (not shown in FIG. 1). The first connector member can be fixedly or removably coupled to the first panel 128 and the second connector member can be fixedly or removably coupled to the second panel member 130. For example, in some embodiments, the connector 126 can be coupled to the first panel 128 and to the second panel 130 with screws, bolts, pins, and/or other known fastening methods. The first connector member and the second connector member can be coupled together with, for example, VELCRO, snaps, buttons, magnet couplings, pins, etc. Thus, the first connector member and the second connector member can couple the first panel member 128 to the second panel member 130. The coupling of the first connector member to the second connector member can be adjustable such that the first panel member 128 and the second panel member 130 can be adjustably coupled together at a selected distance apart from each other. In some embodiments, the first connector member is slidably couplable to the second connector member. In some embodiments, the first connector member or the second connector member includes openings to selectively receive a pin disposed on the other connector member. In some embodiments, a locking pin can also be included to prevent the first connector member and the second connector member form moving relative to each other.

The orthosis device 120 can also include a visual locator (not shown in FIG. 1). For example, a visual locator can be disposed on the first orthosis member 128 and/or the second orthosis member 130 and/or the connector 126. The visual locator can be for example, a mark, a cutout, a separate element coupled to the orthosis device 120, etc. The visual locator can be used to align the orthosis device 120 on the limb of the patient as described in more detail below with reference to embodiments.

The first orthosis member 122 and/or the second orthosis member 124 can include a cradle configured to receive the stimulator unit 102. In some embodiments, the stimulator unit 102 can be coupled to the cradle with a snap-fit coupling such that the stimulator unit 102 can be removed from the orthosis member as needed. The stimulator unit 102 can be used to generate and send a signal to the electrode(s) 132 and/or the electrode(s) 134 to stimulate a portion of the patient's body. In some embodiments, the stimulator unit 102 can send a signal to the electrode(s) 132 and/or the electrode(s) 134 with a wired connection. For example, the stimulator unit 102 can be operatively connected to the first electrode(s) 132 on the first orthosis member 122 and the connector 126 can include an electrical conductor operatively coupling the first electrode(s) 132 and/or the stimulator unit 102 to the electrode(s) 134 on the second orthosis member 124. In some embodiments, the stimulator unit 102 can communicate with the electrode(s) 132 and/or the electrode(s) 134 with a radio frequency (RF) signal. The stimulator unit 102 can receive a signal from the control unit 106 and/or the gait sensor 104 to turn the stimulation on and off. The stimulator unit 102 can include a rechargeable battery and indicator lights (each not shown in FIG. 1), such as a status light and a stimulation light. The stimulator unit 102 can include a port to receive a charging unit (not shown), such as an AC adapter, to charge a rechargeable battery. The stimulator unit 102 can be configured to emit both visual and audio alerts.

In some embodiments, the stimulator unit 102 can include a microprocessor, such as, for example, an application-specific integrated circuit (ASIC) or a combination of ASICs, which are designed to perform one or more specific functions. In some embodiments, the stimulator unit 102 can include an analog or digital circuit, or a combination of multiple circuits. In some embodiments, the stimulator unit 102 can include a memory, such as, for example, a read only memory (ROM) component, a random access memory (RAM) component, electronically programmable read only memory (EPROM), erasable electronically programmable read only memory (EEPROM), and/or flash memory.

In some embodiments, the stimulator unit 102 can include a circuit with a certain arrangement of capacitors such that the circuit can store an amount of energy. In this manner, the stimulator unit 102 can use the energy stored within the capacitors to generate an electrical signal to facilitate the stimulation of a target tissue within the body. As a result of the stored energy in the electronic circuit, stimulation of a target tissue within the body can continue without interruption when energy from the energy source is unavailable due to, for example, maintenance.

The gait sensor 104 can include, for example, a pressure sensor (not shown in FIG. 1) and a transmitter (not shown in FIG. 1) that can communicate wirelessly with the stimulator unit 102. The pressure sensor can detect when the patient's foot is in the air and when it is on the ground. The transmitter can send a signal to the stimulator unit 102 to cause the electrodes to operate to move the foot and knee accordingly. The pressure sensor can be positioned under the insole of the shoe to be worn by the patient on the affected leg to be treated, and can be attached to a gait sensor pad (not shown in FIG. 1). In some embodiments, the gait sensor can be positioned under the insole of the shoe on the unaffected leg. The transmitter can be worn clamped to an inner rim of the patient's shoe. The gait sensor 104 can also optionally include a shoe spacer that can be used to protect the shoe from possible damage from the clamp used to couple the transmitter to the patient's shoe. The gait sensor 104 can be transferred between different shoes (e.g., different styles, right or left). The gait sensor 104 can be powered with, for example, a non-rechargeable or disposable battery. Other examples of a gait sensor that can be used with the orthosis system 100 are described, for example, in International Patent Publication No. WO 03/051453, incorporated herein by reference in its entirety.

The control unit 106 can be used, for example, to turn the orthosis device 120 on and off, to select an operating mode (e.g., gait, training, or standby), fine-tune stimulation intensity, mute audio alerts, test stimulation in the orthosis members 122 and 124, and/or to monitor system performance. The control unit 106 can communicate wirelessly with the stimulator unit 102.

The control unit 106 can be powered with a disposable or rechargeable battery and can include a port to receive a charging unit (not shown), such as an AC adapter, to charge a rechargeable battery. The control unit 106 can be sized such that the control unit 106 can be worn around the neck or wrist of a patient, or carried in a pocket or belt pouch of the patient. For example, the control unit 106 can include a coupling mechanism to couple a lanyard or strap thereto. The control unit 106 can also include user interface features such as, for example, a visual display (e.g., a digital display) and/or indicator lights. For example, the control unit 106 can include a display and indicator lights to indicate various operating conditions, such as, for example, stimulation intensity level, operating mode, battery charge status, electronic registration status, error messages, etc. The control unit 106 can also include audio indicators to indicate, for example, when the system is on, when a button has been pressed, when a low battery is present, and/or an error is present.

In some embodiments, control unit 106 and the gait sensor can be used in conjunction with multiple orthosis members. For example, the control unit 106 and the gait sensor 104 can be configured to communicate with and operate the stimulator unit 102 on the orthosis device 120 and also communicate with and operate another stimulator unit of another orthosis device (not shown in FIG. 1) configured to stimulate another portion of the patient's body. For example, the orthosis device 120 can be coupled to a patient's thigh and another orthosis member can be coupled adjacent to the patient's knee, and the gait sensor 104 and the control unit 106 can be used to operate both the orthosis member 120 and the other orthosis member. Examples of other stimulation systems that can be used to activate the functional electrical stimulation of the orthosis device 120 and examples of other orthosis devices that can be used in conjunction with the orthosis device 120 are described, for example, in International Patent Publication No. WO 03/051453, incorporated by reference above.

The orthosis device 120 can be used in the functional electrical stimulation treatment of various locations on a patient's body, such as for example, a leg or arm. The orthosis device 120 can be used for the functional electrical stimulation treatment of various nerves and/or muscles or muscle groups on a particular limb. As described above, a distance between the first panel 128 and the second panel 130 can be adjusted with the connector 126 to fit the particular limb to which treatment is to be applied.

In one example use, the orthosis device 120 can be disposed about a first portion of a thigh of a patient such that the electrode(s) 132 on the first panel 128 and the electrode(s) 134 on the second panel 130 can each stimulate a different portion of a hamstring muscle of the patient. The patient can reposition the orthosis 120 on the thigh such that the electrode(s) 132 on the first panel 128 and the electrode(s) 134 on the second panel 130 can each stimulate a different portion of the thigh. For example, the orthosis 120 can be disposed about a first portion of a thigh of a patient such that the electrode(s) 132 on the first panel 128 and the electrode(s) 134 on the second panel 130 can each stimulate a different portion of a quadriceps muscle or quadriceps muscle group and/or the nerves associated with those muscles of the patient. In another example, both the first panel 128 and the second panel 130 can both be configured to stimulate different portions of a hamstring muscle or the nerves associated with the hamstring muscle. In some embodiments, the first panel 128 can be configured to stimulate the quadriceps and the second panel 130 can be configured to stimulate the hamstring muscle. In some embodiments, the first panel 128 can be disposed adjacent the upper portion of the leg and the second panel 130 can be disposed about the lower portion of the leg.

In another example use, the orthosis device 120 can be disposed about an arm of a patient such that the electrode(s) 132 on the first panel 128 and the electrode(s) 134 on the second panel 130 can each stimulate a different muscle portion of the arm of the patient and/or the nerves associated with those muscles of the patient. For example, in one example use, the orthosis device 120 can be disposed about a forearm portion such that at least a portion of the electrode(s) 132 is configured to stimulate at least one of a flexor muscle located in the forearm and at least a portion of the electrode(s) 134 can stimulate at least one of the extensor muscles located in the forearm.

Figure 2:
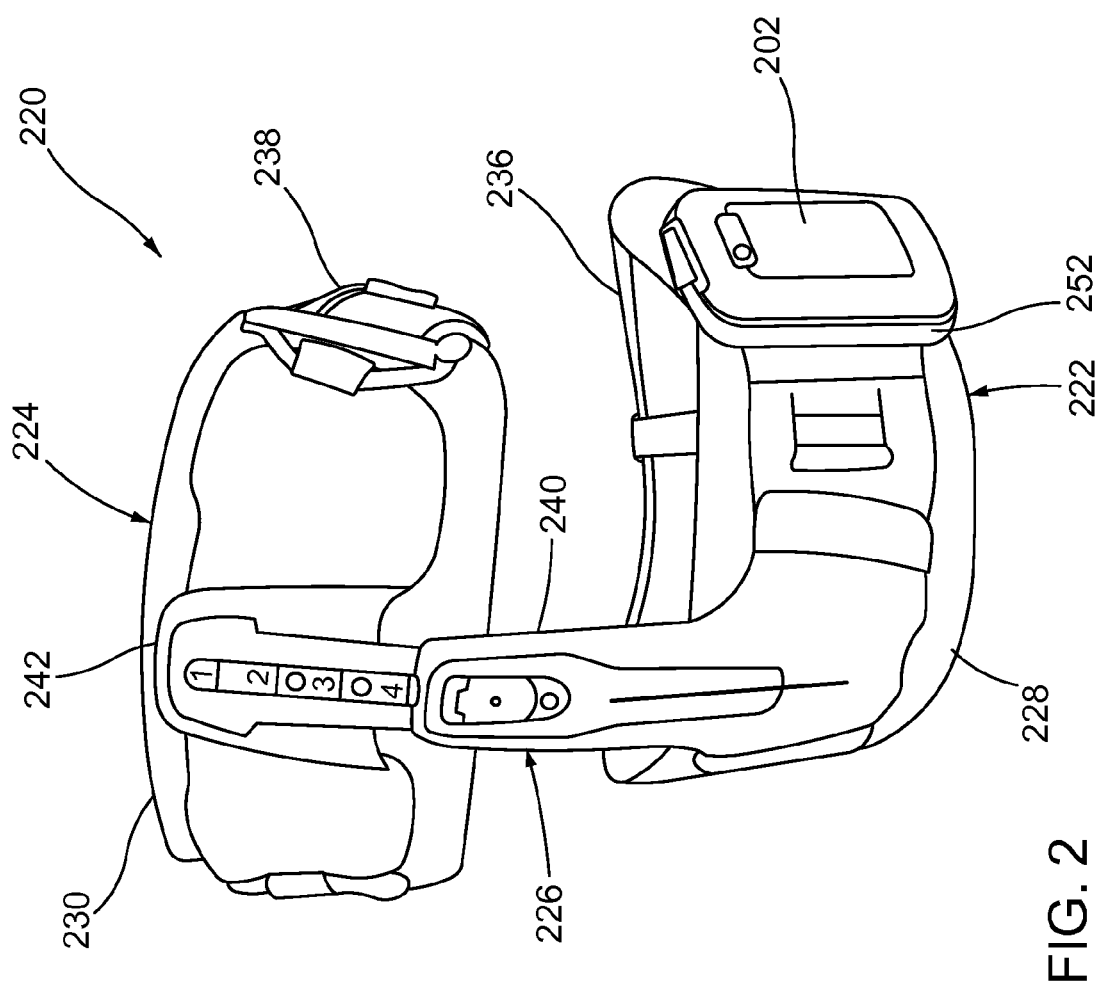
FIG. 2 is a front perspective view of an orthosis device according to an embodiment.
Figure 3:
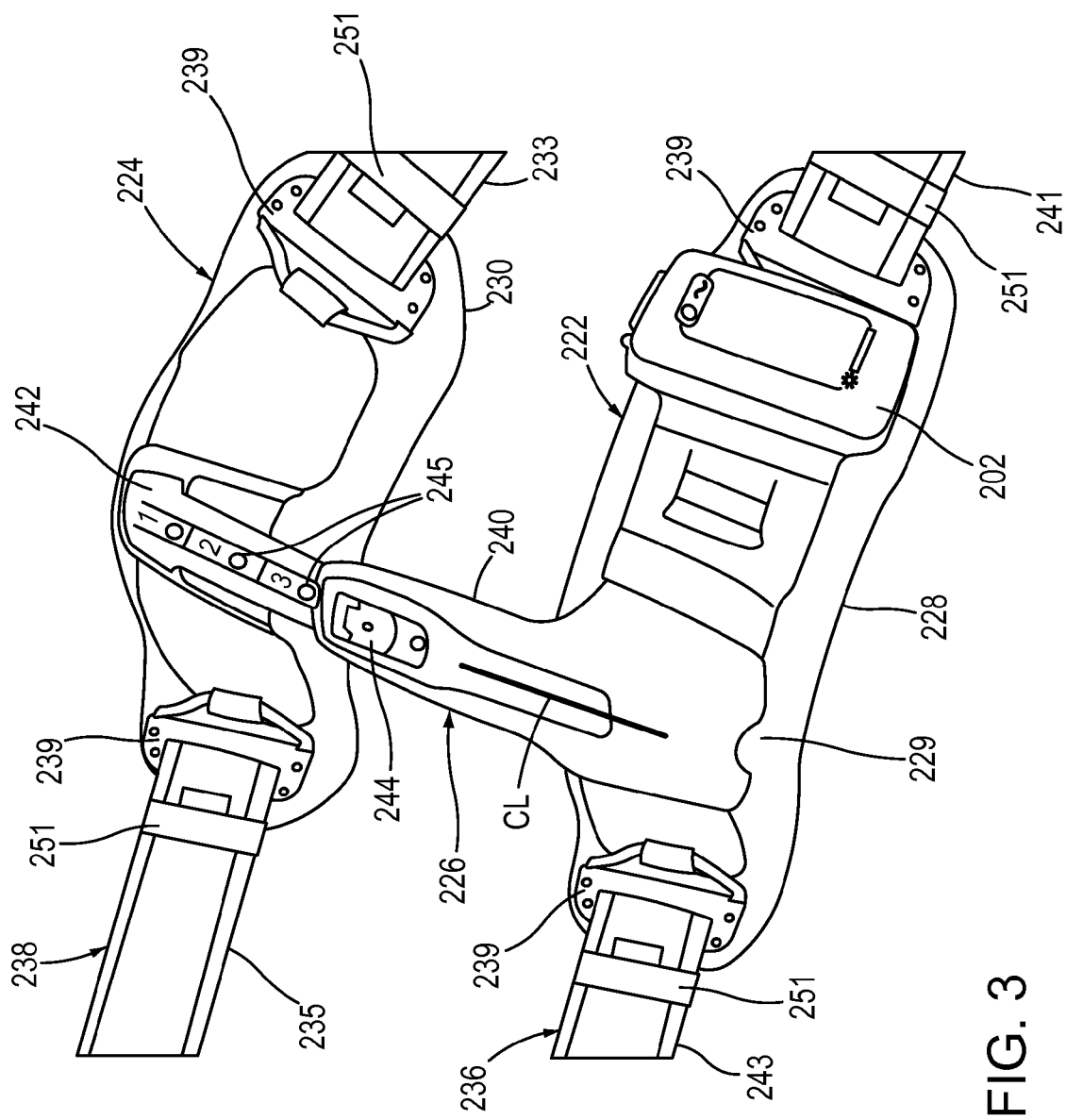
FIG. 3 is a front perspective view of a portion of the orthosis device of FIG. 2.

FIGS. 2 and 3 illustrate an orthosis device according to an embodiment. The orthosis device 220 includes a first orthosis member 222, a second orthosis member 224, a connector 226 and a stimulator unit 202. As described above for orthosis device 120, the orthosis device 220 can be used to provide electrical stimulation to a portion of a limb of a patient, such as for example, an arm or a leg of the patient. For example, the orthosis device 220 can be disposed on a thigh of a patient such that the first orthosis member 222 is disposed at a first distance from the knee of the patient and the second orthosis member 224 is disposed at a second distance from the knee that is greater than the first distance.

Figure 4A:
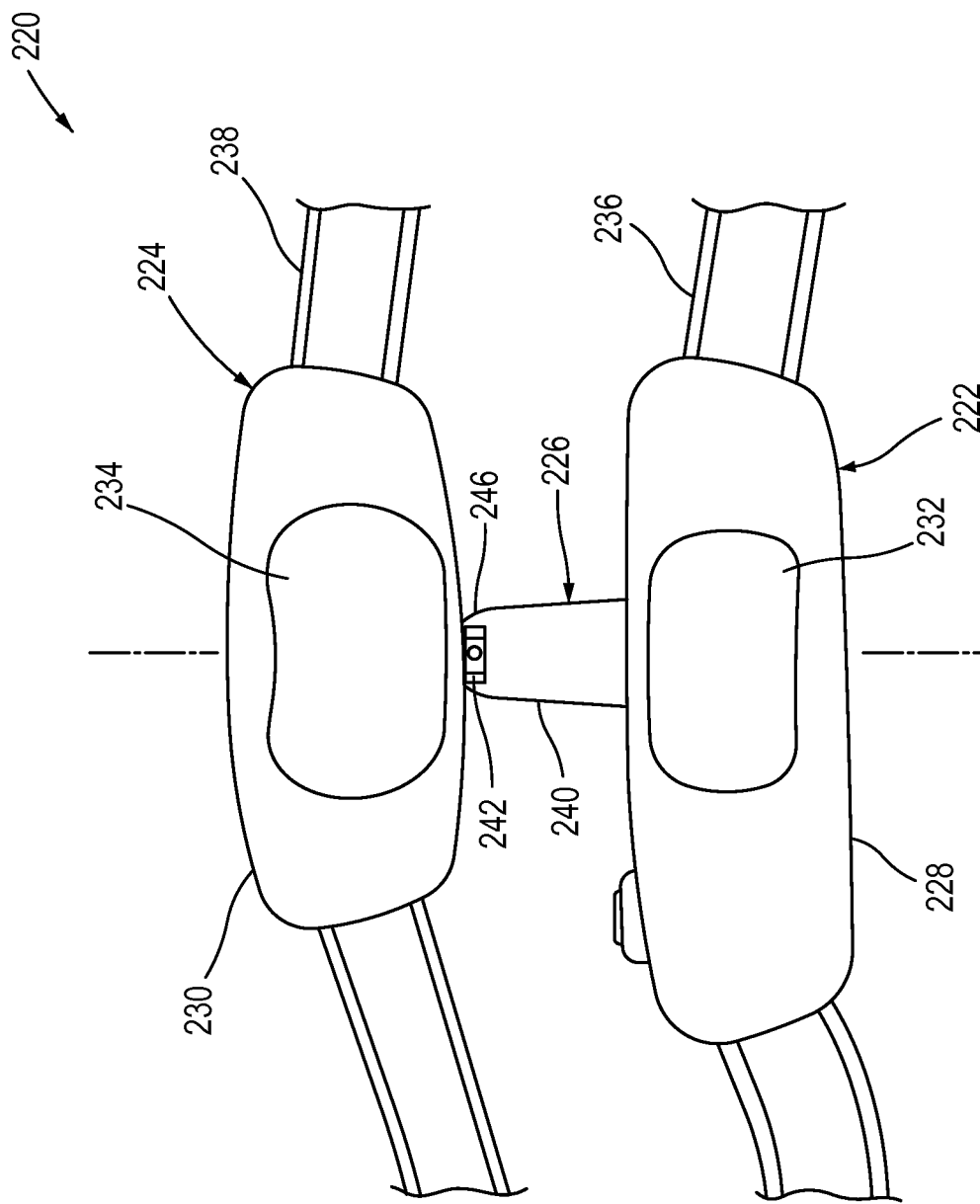
FIG. 4A is a back view of a portion of the orthosis device of FIG. 2 shown with an electrode positioned at a first location on the orthosis device.

The first orthosis member 222 includes a first panel or cuff 228 and a first strap assembly 236, and the second orthosis member 224 includes a second panel or cuff 230 and a second strap assembly 238. As shown in FIGS. 4A and 4B, a first electrode 232 can be removably coupled to an inner surface of the panel 228 and a second electrode 234 can be removably coupled to an inner surface of the second panel 230. The first orthosis member 222 and the second orthosis member 224 are each configured to be coupled to a limb of a patient such that the first electrode 232 and the second electrode 234 can each contact the skin of the patient. The first electrode 232 can be disposed off-set from a center-line CL defined by the connector 226 as shown in FIG. 4B, or substantially aligned or centered with the center-line CL of the connector 226 as shown in FIG. 4A.

Figure 5:
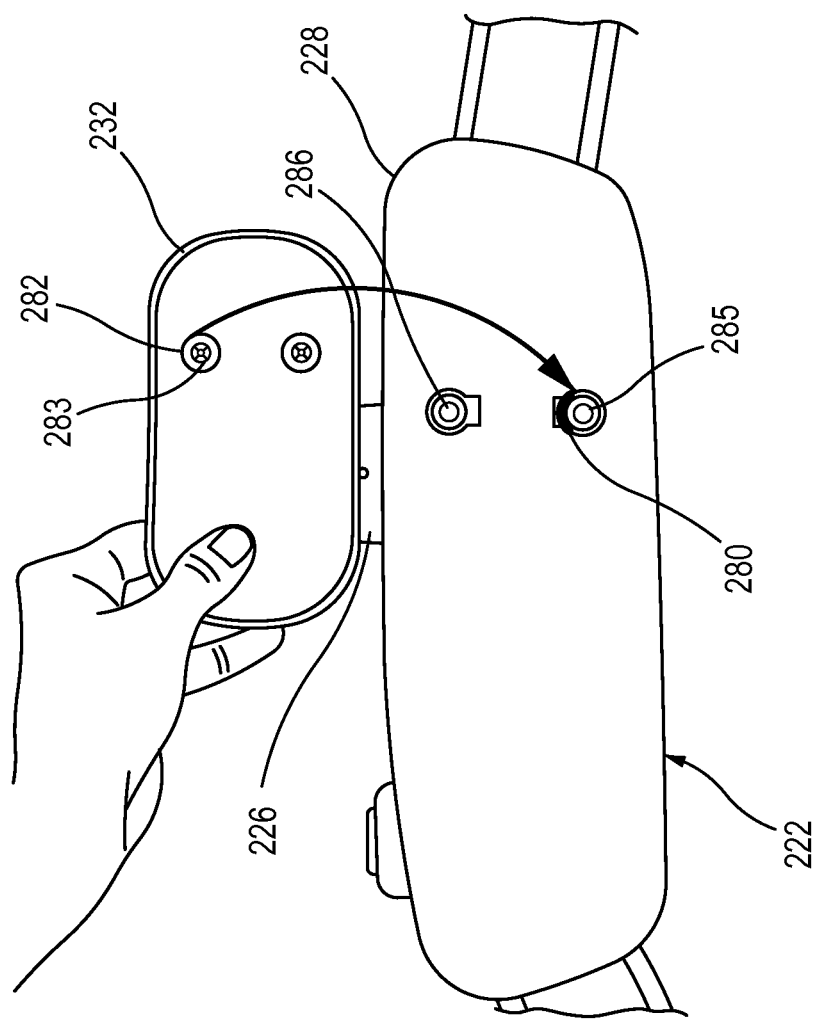
FIG. 5 is a back view of a portion of the orthosis device of FIG. 2 illustrating the coupling of an electrode.
Figure 6:
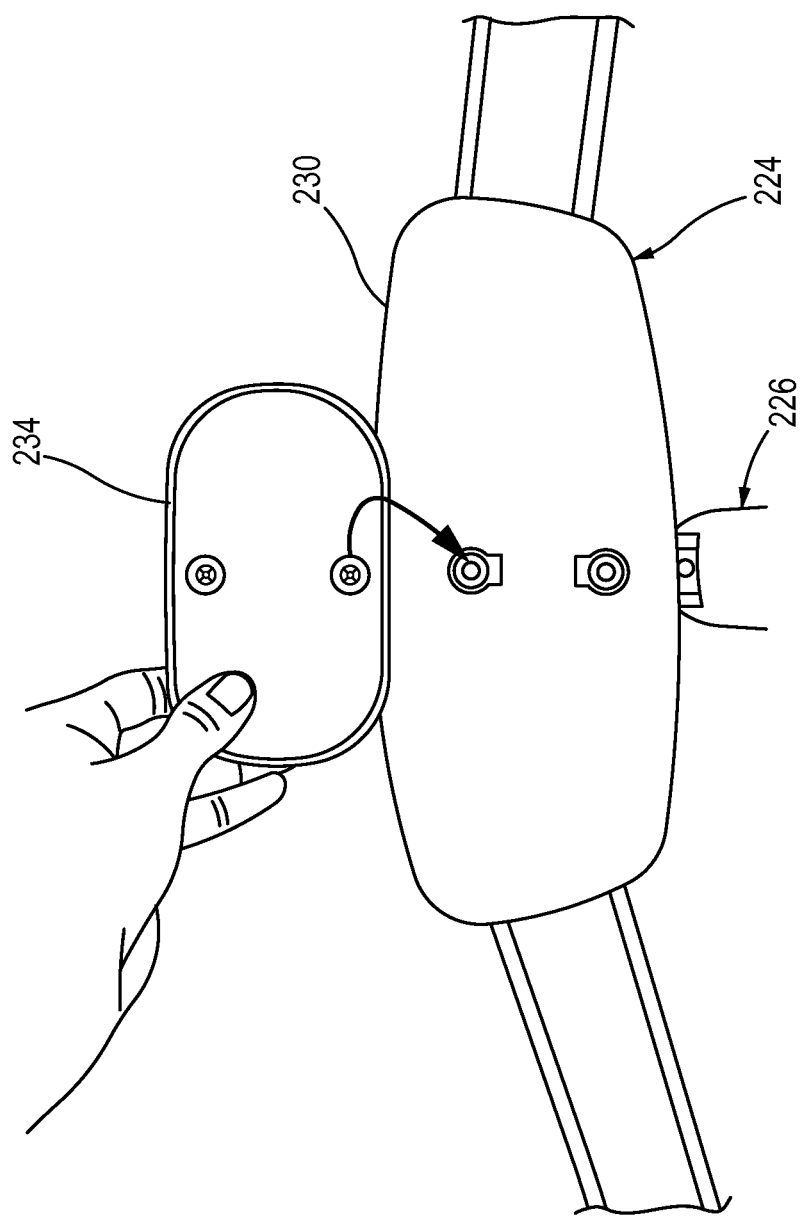
FIG. 6 is a back view of a portion of the orthosis device of FIG. 2 illustrating the coupling of an electrode.

The first electrode 232 and the second electrode 234 can each be removably coupled to the first panel 228 and the second panel 230, respectively, with a snap-fit coupling, as shown in FIGS. 5 and 6. While conventional snap-fit couplings are illustrated, in some embodiments, the couplings may be uniquely shaped to ensure the use of the appropriate electrodes. In some embodiments, each of the snap-fit couplings may be different shapes to ensure the correct electrode is placed on the correct panel. In some embodiments, as shown in FIG. 5, the first panel 228 can include a locator marking 280 on a snap coupling 285, and the first electrode 232 can include a corresponding marking 282 disposed on a snap 283. The locator marking 280 indicates that the first electrode 232 is to be positioned on the first panel 228 with the snap 283 on the first electrode 232 snap-fit to the snap coupling 285 on the panel 228. For example, a clinician can pre-fit the orthosis device 220 for the particular patient and particular treatment and place the locator marker 280 on the first panel 228 and the marker 282 on the electrode 232. In this embodiment, the locator marker 280 indicates that the first electrode 232 is to be placed in a centered position relative to the centerline CL (e.g., as shown in FIG. 4A) of the connector 226. If the first electrode 232 is to be positioned in an off-centered position (e.g., as shown in FIG. 4B) on the panel 228, the locator marker 280 would be disposed on the snap coupling 286 on the first panel 228 and the first electrode 232 would be re-oriented (e.g., rotated 90 degrees) such that the snap 283 or the other snap on the first electrode 232 could be snap-fit to the snap coupling 286.

Similarly, as shown in FIG. 6, the second electrode 234 can be snap-fit to the second panel 230 using similar snap-fit couplings. In this embodiment, the snaps on the second electrode 234 are centered, and thus the second electrode 234 can only be oriented in a centered position. It should be understood, however, that in alternative embodiments, the snaps on the second electrode 234 can be configured similar to the first electrode 232 to allow the second electrode 234 to be placed in multiple positions on the second panel 230. In some embodiments, multiple snap couplings may be provided on each of the panels 228, 230 to provide for multiple possible orientations of the electrodes 232, 234.

Figure 7:
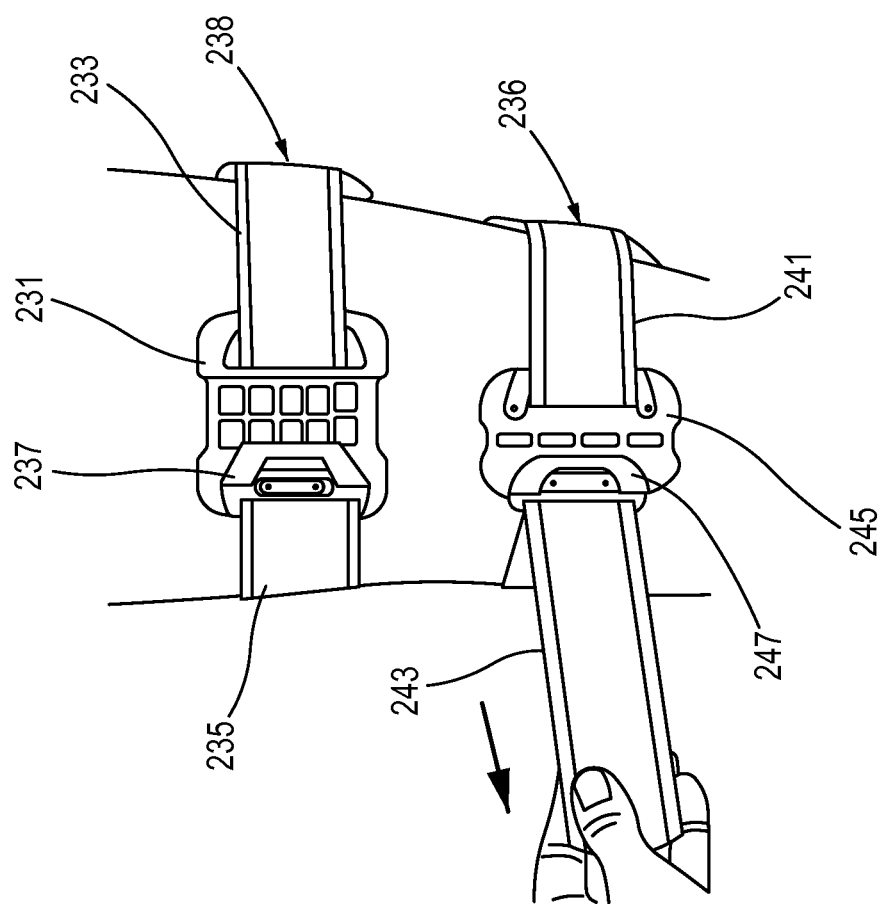
FIG. 7 is a front view of a limb of a patient with the orthosis device of FIG. 2 disposed thereon in a first position.

The first strap assembly 236 and the second strap assembly 238 are each adjustable such that the orthosis device 220 can be adjustably sized to fit a particular limb and/or particular patient. The strap assembly 236 includes a first strap member 241 and a second strap member 243 as shown, for example, in FIG. 7. The first strap member 241 and the second strap member 243 can each be coupled to a strap lead 239 (shown in FIG. 3) disposed on the first panel 228. Any excess strap can be looped thorough a strap attachment element 251 (shown in FIG. 3) disposed on each of the first strap member 241 and the second strap member 243. A buckle 245 is coupled to an end of the first strap member 241 and a magnetic coupling element 247 is coupled to an end of the second strap member 243. As shown in FIG. 7, the magnetic coupling element 247 can be magnetically coupled to the buckle 245.

Similarly, the strap assembly 238 includes a third strap member 233 and a fourth strap member 235 as shown, for example, in FIG. 7. The third strap member 233 and the fourth strap member 235 can each be coupled to a strap lead 239 (shown in FIG. 3) disposed on the second panel 230. Any excess strap can be looped thorough a strap attachment element 251 (shown in FIG. 3) disposed on each of the third strap member 233 and the fourth strap member 235. A buckle 231 is coupled to an end of the third strap member 233 and a magnetic coupling element 237 is coupled to an end of the fourth strap member 235. As shown in FIG. 7, the magnetic coupling element 237 can be magnetically coupled to the buckle 237.

The orthosis device 220 also includes a visual locator 229 disposed on the connector 226, as shown, for example, in FIG. 3. In this embodiment, the visual locator 229 is in the form of a cutout defined at the centerline CL of the connector 226. The visual locator 229 can be used to help position the orthosis device 220 on a limb of a patient as described in more detail below.

In some embodiments, the connector 226 includes a first connector member 240 and a second connector member 242. The first connector member 240 can be removably or fixedly coupled to the first orthosis member 222 with, for example, screws, bolts, pins, or other known coupling methods. Similarly, the second connector member 242 can be removably or fixedly coupled to the second orthosis member 224 with, for example, screws, bolts, pins, or other known fastening methods. The first connector member 240 can be slidably and adjustably coupled to the second connector member 242 to selectively adjust a distance or length between the first orthosis member 222 and the second orthosis member 224 (and first panel 228 and second panel 230). As shown, for example, in FIGS. 4A and 4B, the second connector member 242 can be slidably received within a pocket 246 defined in the first connector member 240.

Figure 8:
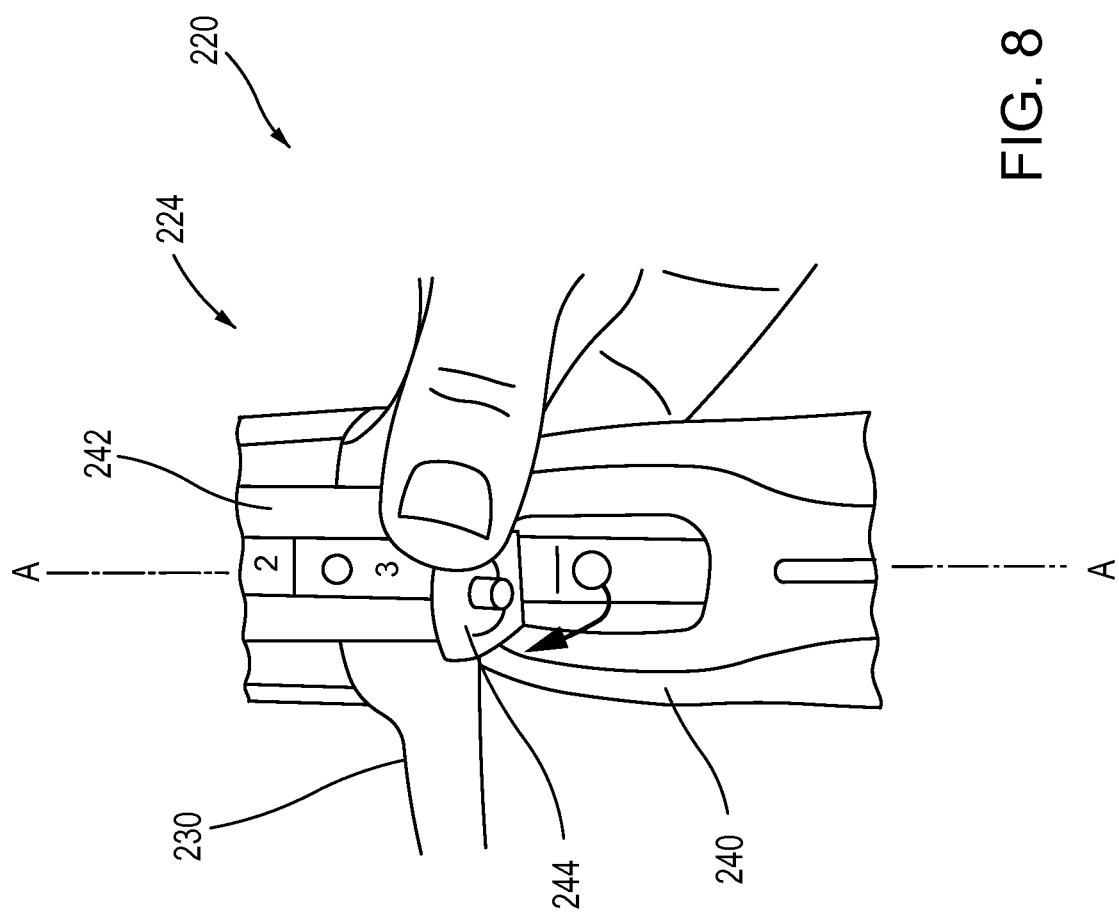
FIG. 8 is a front view of a portion of the orthosis device of FIG. 2.
Figure 9:
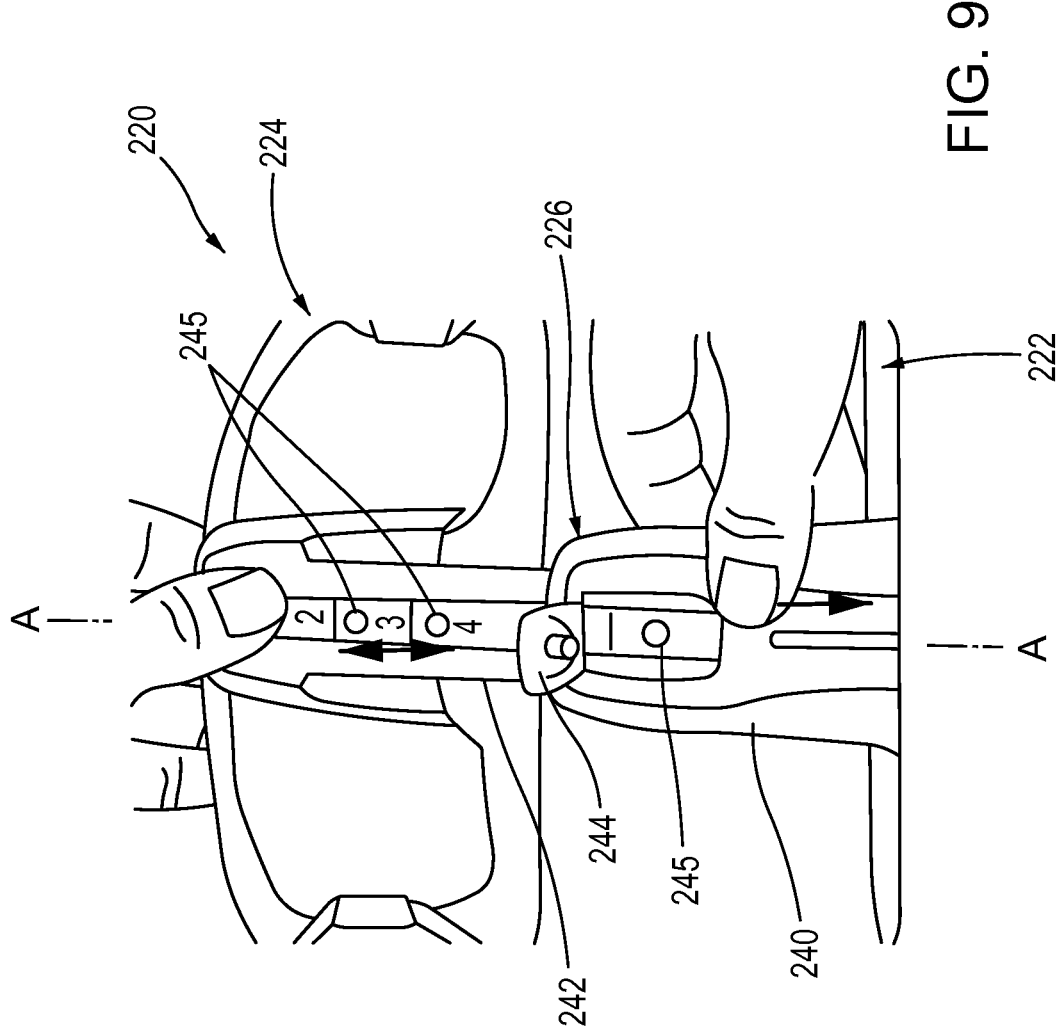
FIG. 9 is a front view of a portion of the orthosis device of FIG. 2.
Figure 10:
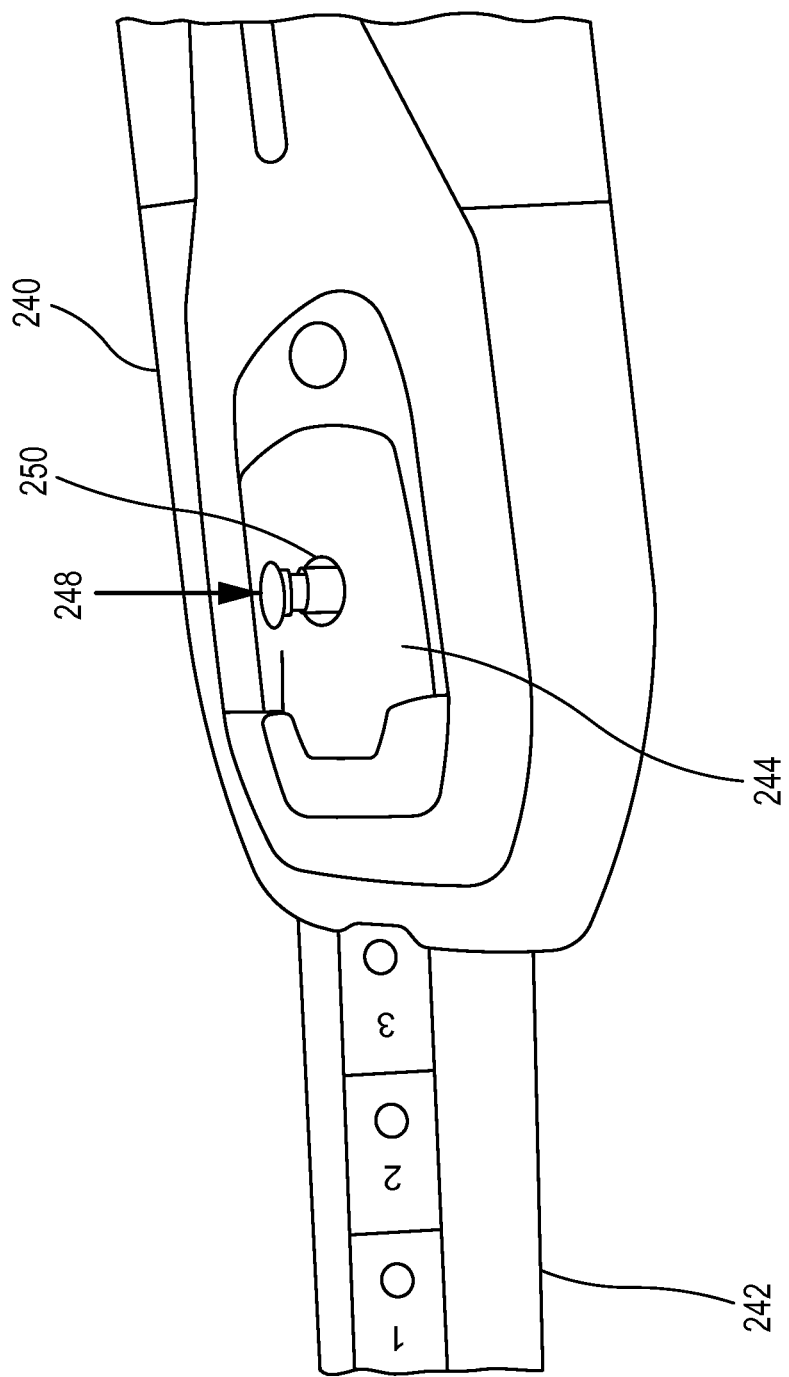
FIG. 10 is a side perspective view of a portion of the connector of the orthosis device of FIG. 2.

To adjust the distance or length between the first orthosis member 222 and the second orthosis member 224, a hinge pin 244 on the first connector member 240 (see e.g., FIGS. 8 and 9) is uncoupled to allow the second connector member 242 to slidably move within the pocket 244 of the first connector member 240. The first connector member 240 and the second connector member 242 are moved either toward or away from each other until a desired length is achieved (see, e.g., FIG. 9). The hinge-pin 244 is then inserted and snapped into an opening 245 in the second connector member 242 at the desired length. To lock the first connector 240 and the second connector 242 at the desired length, a locking pin 248 can be inserted into an opening 250 defined in the first connector member 240 as shown in FIG. 10. When the locking pin 248 is in place, the connector 226 (i.e., the first connector member 240 and the second connector member 242) can limit movement of the second panel 230 and the first panel 228 relative to each other in a direction along a longitudinal axis A of the connector 226 (see e.g., FIGS. 8 and 9). Thus, the connector 226 can limit movement of the first orthosis member 222 and the second orthosis member 224 relative to each other along a longitudinal axis of the limb on which the orthosis device 220 is coupled. In some embodiments, the first connector member 240 and second connector member 242 are locked in place by other known means such as, for example, a friction fit. In some embodiments the first connector member 240 and second connector member 242 are arranged in a telescoping manner and can be locked in place relative to one another.

In some embodiments, the first orthosis member 222 and the second orthosis member 224 can slide relative to the connector 226 (i.e., the first connector member 240 and the second connector member 242) to change the relative position of the orthosis members 222, 224. In some embodiments, the connector member 226 can be a unitary or monolithic construction along which the first orthosis member 222 and the second orthosis member 224 can be positioned.

Figure 11:
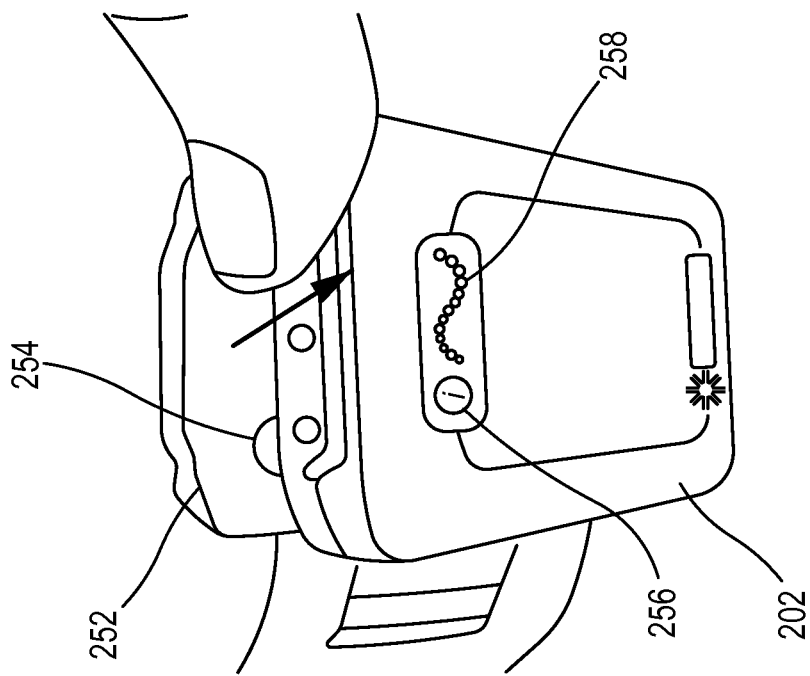
FIG. 11 is a perspective view of a portion of the orthosis device of FIG. 2.

The orthosis member 222 also includes a cradle 252 or receiving portion configured to couple the stimulator unit 202 thereto. The stimulator unit 202 can be removably coupled to the cradle 252 with a snap-fit connection. As shown in FIG. 11, the cradle 252 can include a snap connector configured to receive a mating sap fit connector (not shown) on the stimulator unit 202. The stimulator unit 202 can include any of the features and functions as described above for stimulator 102. The stimulator unit 202 can be used to generate and send a signal to the electrode 232 and the electrode 234 to stimulate a portion of the patient's body. The stimulator unit 202 can include a radio frequency (RF) transmitter and communicate with the electrodes 232 and 234 with a RF signal. The stimulator unit 202 can be powered with a rechargeable battery (not shown) and includes a status light 256 and a stimulation light 258 (see e.g., FIG. 11). The stimulator unit 202 can emit both visual and audio alerts or indications. For example, the stimulator unit 202 can indicate if the radio communication malfunctions. The stimulator unit 202 can receive a wireless signal from a control unit 206 (described below) and a gait sensor 204 (described below) to turn the stimulation on and off and actuate the stimulation.

The control unit 206 (see e.g., FIG. 12) can be used to control operation of the orthosis device 220. The control unit 206 can communicate wirelessly with the gait sensor 204 and the stimulator unit 202. The control unit 206 can be used, for example, to turn the orthosis device 220 on and off, to select an operating mode (e.g., gait, training, or standby), fine-tune stimulation intensity, mute audio alerts, test stimulation in the orthosis members 222 and 224, and/or to monitor system performance. The control unit 206 can also communicate wirelessly with the stimulator 202.

The control unit 206 can be powered with a disposable or rechargeable battery (not shown) and can be sized such that the control unit 206 can be worn around the neck or wrist of a patient, clipped to the belt of a patient or carried in a pocket of a belt pouch of the patient. For example, the control unit 206 can include an attachment mechanism, such as a clip or loop or hook (not shown) to couple a lanyard or strap thereto. The control unit 206 can include various user interfaces and operating controls. For example, as shown in FIG. 12, the control unit 206 includes, for example, an on-off button 268, +/− intensity adjustment buttons 269, a mode button 270, a stimulation test button 271, stimulator selection buttons 272, and a mute button 273. The various buttons are configured to actuate the control unit to produce the desired effect. The control unit 206 also includes indicators, such as, for example, a digital display 274, a gait sensor indicator 275, stimulation indicator and selection arrows 276, a control unit indicator 277, and a RF communication indicator 278. The various indicators can indicate, for example, stimulation intensity level, operating mode, battery charge status, electronic registration status, error messages, etc. The control unit 206 can also include audio indicators to indicate, for example, when the system is on, a button has been pressed, a low battery is present, and/or an error is present.

Figure 15:
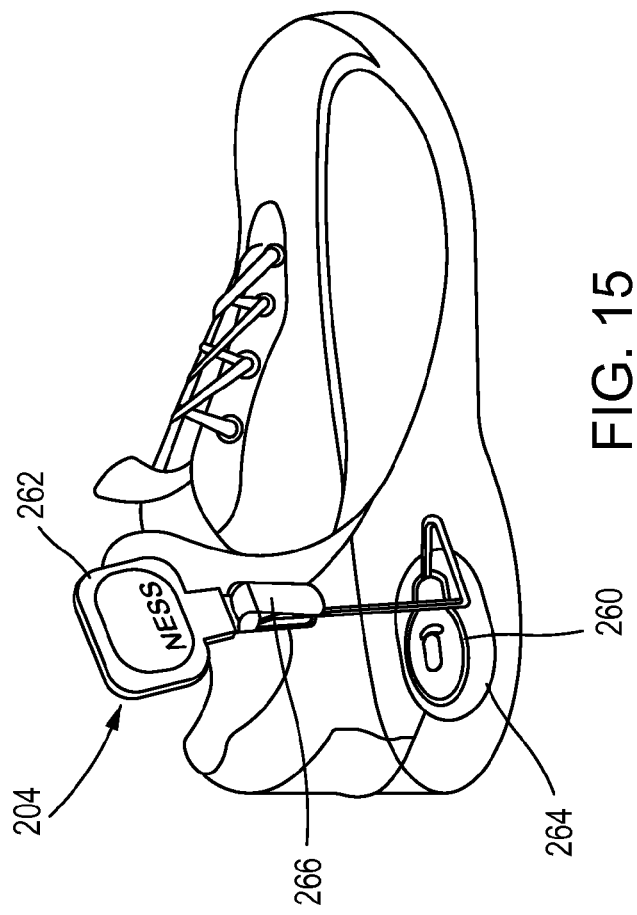
FIG. 15 is a side perspective view of the gait sensor of FIG. 13 and the gait sensor pad of FIG. 14 shown disposed on a shoe according to an embodiment.
Figure 14:
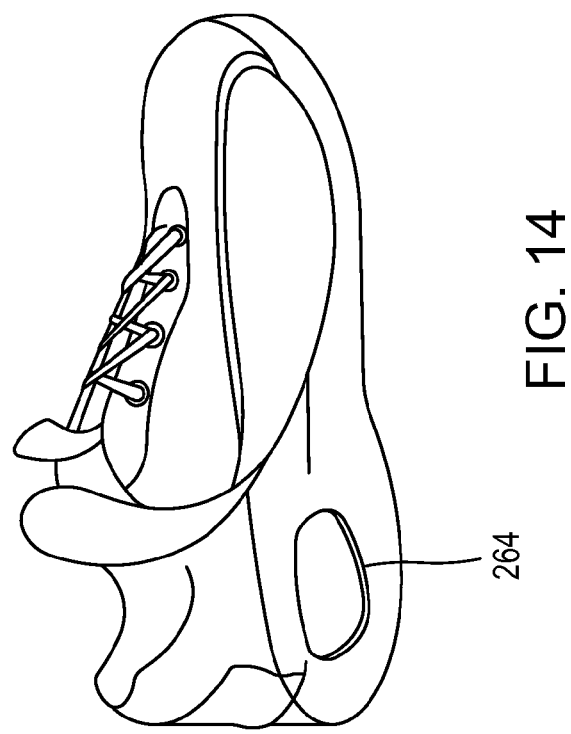
FIG. 14 is a side perspective view of a gait sensor pad disposed within a shoe according to an embodiment.

As shown in FIG. 13, the gait sensor 204 includes a pressure sensor 260 and a transmitter 262. The transmitter 262 can communicate wirelessly with the stimulator unit 202. The pressure sensor 260 can detect when the patient's foot is in the air and when it is on the ground. The transmitter 262 can signal the stimulator unit 202 to move the foot and knee accordingly. A gait sensor pad 264 can be placed on the insole of a shoe to be worn on the foot of an affected leg to be treated (as shown in FIG. 14), and the pressure sensor 260 can be positioned on the sensor pad 264, as shown in FIG. 15.

The gait sensor 204 also includes a clamp 266 to attach the transmitter 262 to an inner rim of the patient's shoe. The gait sensor 204 can also optionally include a shoe spacer (not shown) that can be used to protect the shoe from possible damage from the clamp 266 contacting the shoe. As described previously, the gait sensor 204 can be transferred between different shoes (e.g., different styles, right or left). The gait sensor 204 can be powered by a non-rechargeable or rechargeable battery (not shown).

Figure 16:
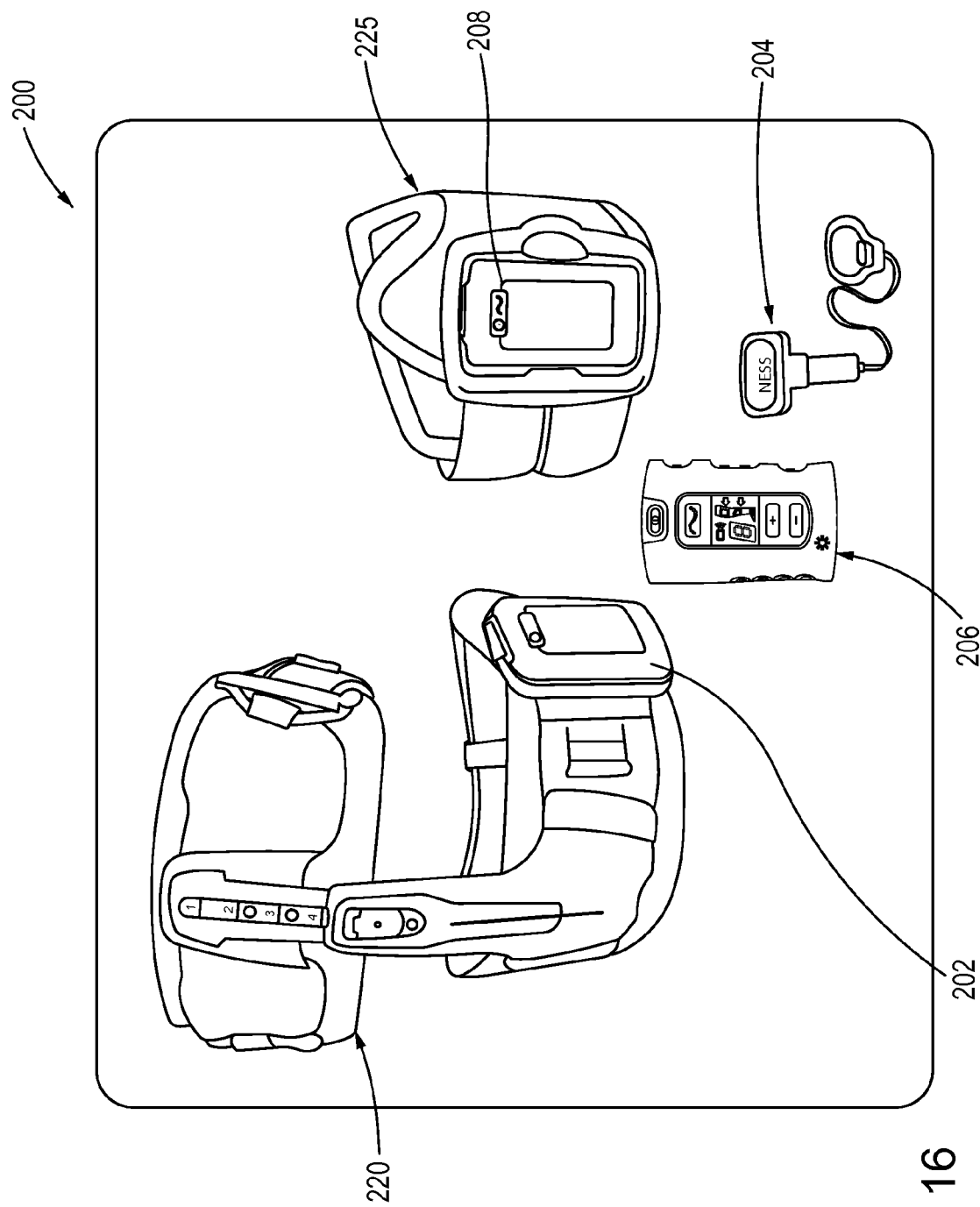
FIG. 16 is a perspective view of an orthosis system according to an embodiment.

As described above the orthosis system 100, the control unit 206 and the gait sensor 204 can each be used in conjunction with multiple orthosis members. For example, the control unit 206 and gait sensor 204 can be configured to communicate with and operate the stimulator 202 of orthosis device 220 and operate a stimulator unit of another orthosis device configured to stimulate another portion of the patient's body. As shown in FIG. 16, the orthosis device 220, the control unit 206, the gait sensor 104 and an orthosis device 225 can be provided as a system 200. Thus, orthosis device 220 can be used in conjunction with the orthosis device 225. The control unit 206 and the gait sensor 104 can each be used to actuate the stimulator unit 202 of the orthosis device 220 and a stimulator unit 208 of the orthosis device 225. For example, as shown in FIG. 12, the control unit 206 includes stimulator selection buttons 272 stimulation indicator and selection arrows 276 that can be used to select and indicate which orthosis device 220 is activated. The orthosis device 225 can include one or more electrodes, and adjustable straps as described above for orthosis device 220. Other types of orthosis can alternatively be used in conjunction with the orthosis device 220. For example, devices described in International Patent Publication No. WO 03/051453 incorporated by reference above can also be used. In some embodiments, a single charger can be used to charge the orthosis device 220, the orthosis device 225, the control unit 206, and/or the gait sensor 204.

Figure 17:
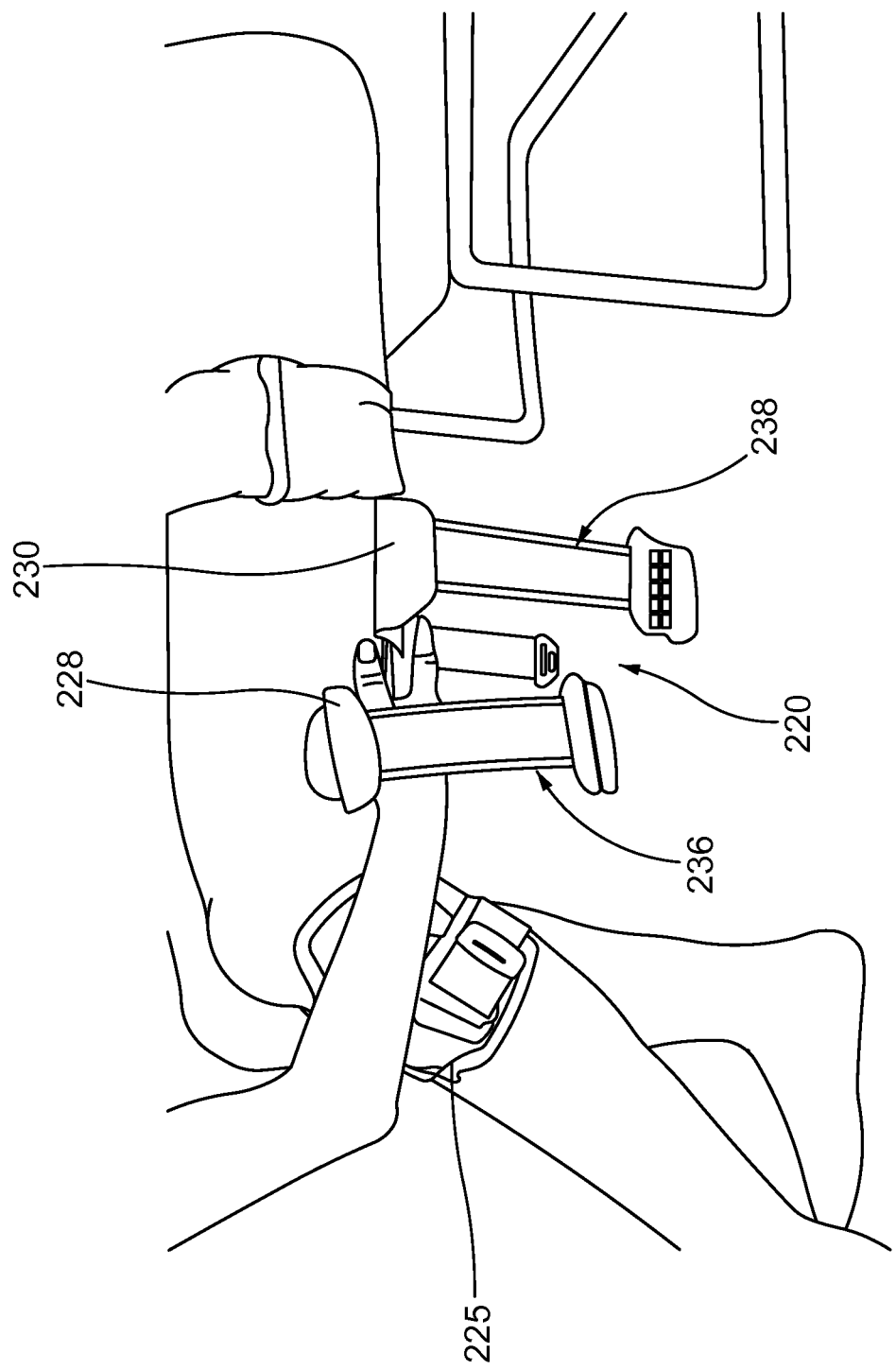
FIG. 17 is a side perspective view illustrating the donning of the orthosis device of FIG. 2 on a leg.
Figure 18:
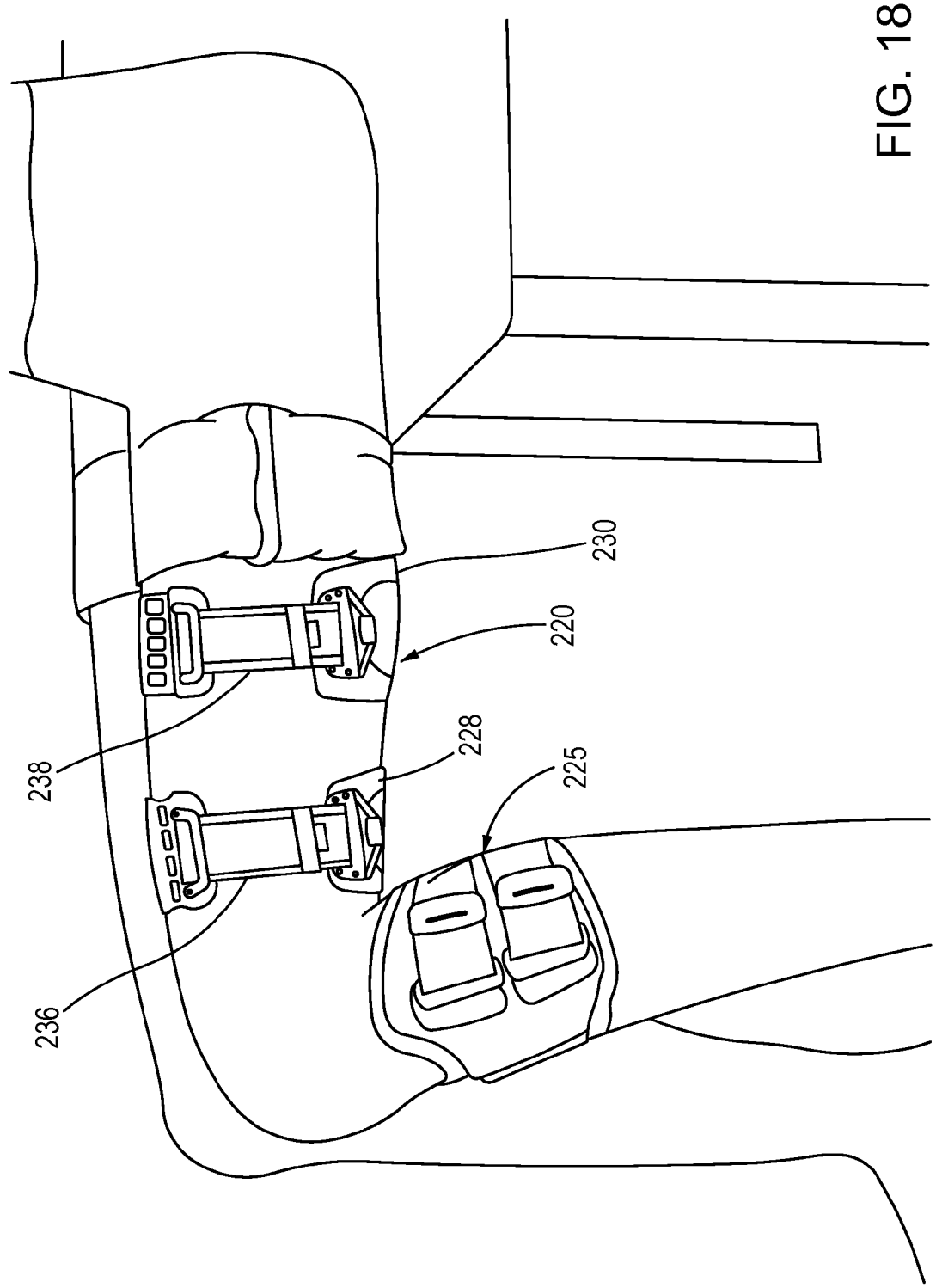
FIG. 18 is a side perspective view illustrating the orthosis device of FIG. 2 disposed on a leg in the first position.
Figure 21:
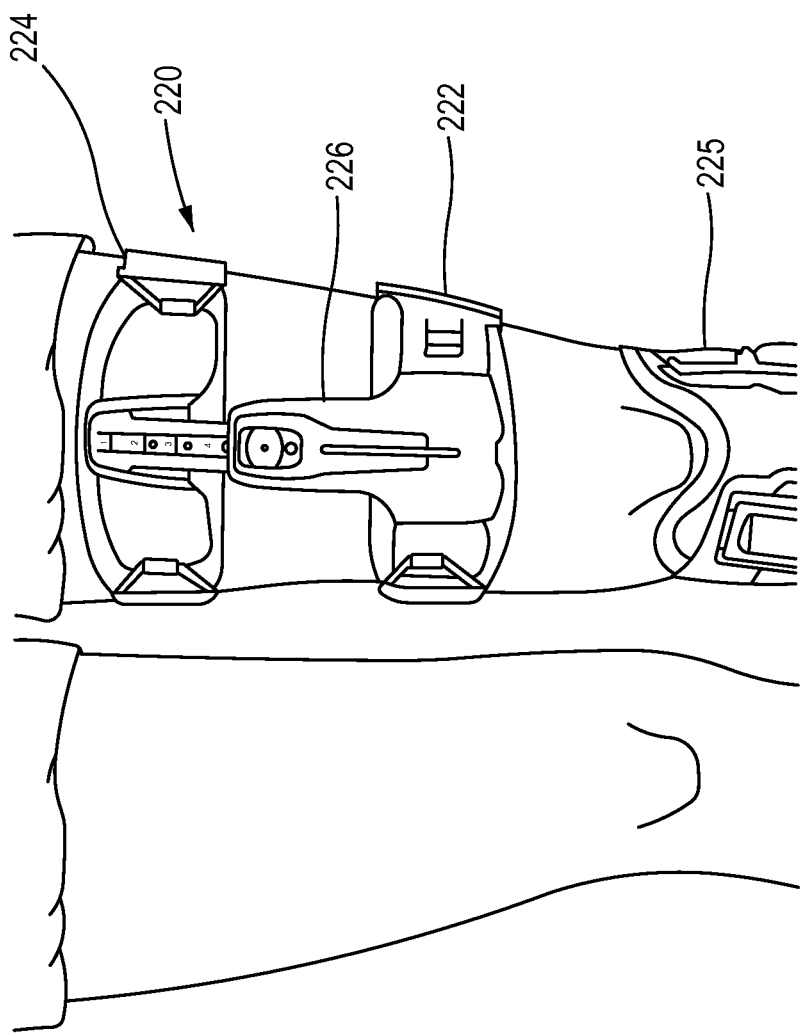
FIG. 21 is a front view illustrating the orthosis device of FIG. 2 disposed on a leg in a second position.
Figure 22:
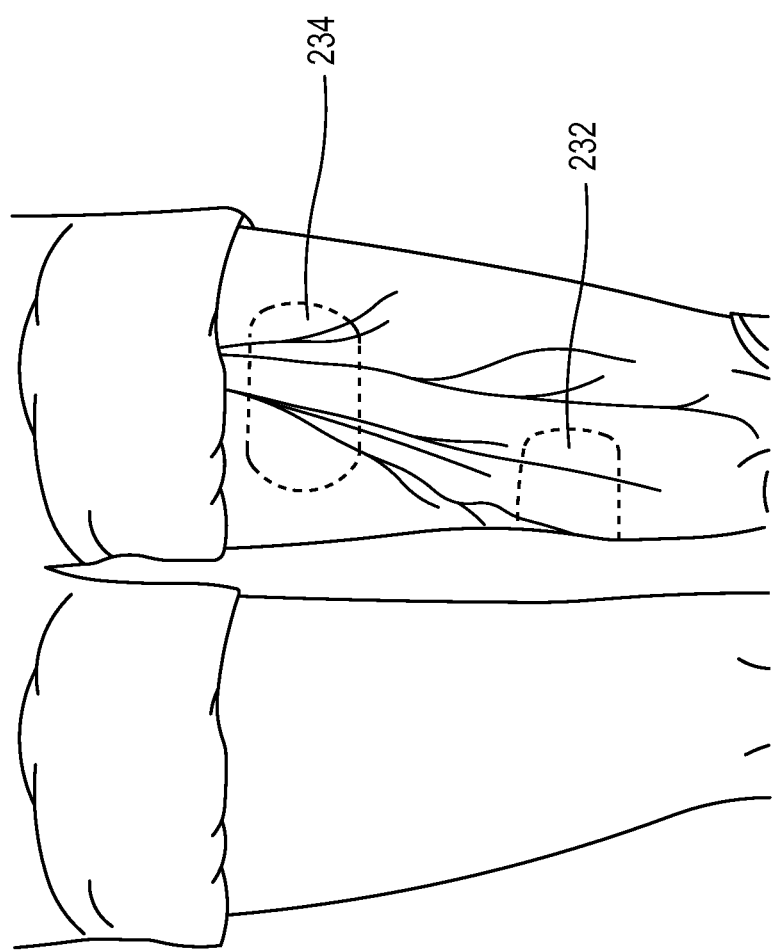
FIG. 22 is a front view of a portion of a patient illustrating the location of electrodes on a quadriceps muscles.

The orthosis device 220 can be used in the functional electrical stimulation treatment of various locations on a patient's body, such as for example, a leg, foot, arm or hand. The orthosis device 220 can be used for the functional electrical stimulation treatment of various muscles or muscle groups on a particular limb. FIGS. 17-22 illustrate the positioning and use of the orthosis device 220 on a leg of a patient and in particular a thigh of the patient. It should be understood, however, that the orthosis device 220 can be configured for use on other portions of a patient's body. FIGS. 17, 18 and 21 also show the orthosis device 225 disposed below a knee of the patient. As described above, although not necessary, the orthosis device 220 can be used in conjunction with the orthosis device 225.

The orthosis device 220 can be used to treat various muscles on a thigh of a patient. The orthosis device 220 can be disposed about a first portion of a thigh of a patient such that the electrode 232 of the first orthosis member 222 contacts the first portion of the thigh and the second electrode 234 of the second orthosis member 224 contacts a second portion of the thigh. The orthosis device 220 can then be repositioned on the thigh of the patient such that the electrode 232 of the first orthosis member 222 contacts the third portion of the thigh and the second electrode 234 of the second orthosis member 224 contacts a fourth portion of the thigh.

Figure 19:
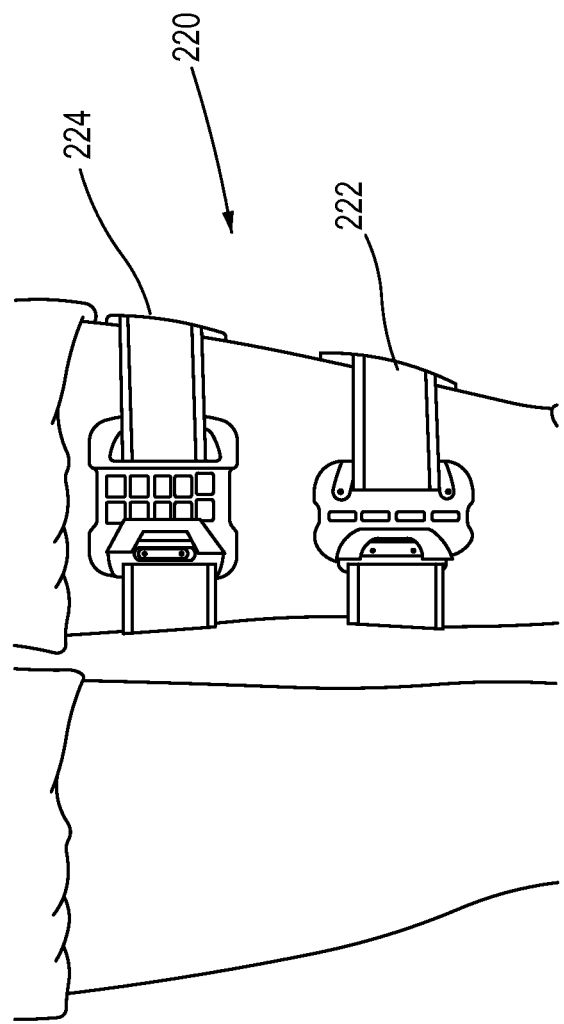
FIG. 19 is a front view illustrating the orthosis device of FIG. 2 disposed on a leg in the first position.
Figure 20:
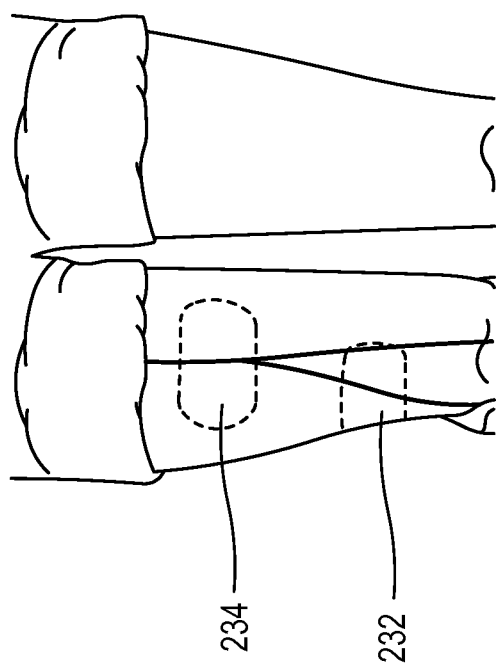
FIG. 20 is a back view of a portion of a patient illustrating the location of electrodes on a hamstring muscles or tendons.

For example, in one use of the orthosis device 220, the first orthosis member 222 is positioned on the thigh of a patient such that the electrode 232 can stimulate a first portion of a hamstring muscle of the patient and the second orthosis member 224 is positioned on the thigh of the patient such that the electrode 234 can stimulate a second portion of the hamstring muscle of the patient. As shown in FIG. 16, with the straps decoupled, a patient can place the orthosis device 220 on a thigh of the patient with the visual locator 229 (not shown in FIG. 16) three finger widths from a back of the patient's knee and such that the connector 226 is positioned centered along a back of the thigh. The magnetic coupling element 237 can be coupled to the buckle 231 on the second orthosis member 224 and the magnetic coupling 247 can be coupled to the buckle 245 on the first orthosis member 222 to secure the orthosis device 220 to the thigh, as shown in FIGS. 17 and 18. In this position, the first electrode 232 can be actuated to stimulate a first portion of a hamstring muscle and the second electrode 234 can be actuated to stimulate a second portion of the hamstring muscle as illustrated in FIG. 19.

The orthosis device 220 can be repositioned for use in treating the quadriceps muscle of the patient. To position the orthosis device 220 to stimulate the quadriceps muscle, the patient can again use the visual locator 229. Specifically, with the straps decoupled, the orthosis device 220 can be placed on the thigh of the patient with the visual locator 229 three finger widths from a top of the patient's knee and such that the connector 226 is centered along a top of the thigh (as shown in 20). As described above, the magnetic coupling element 237 can be coupled to the buckle 231 on the second orthosis member 224 and the magnetic coupling 247 can be coupled to the buckle 245 on the first orthosis member 222 to secure the orthosis device 220 to the thigh. In this position the first electrode 232 can be actuated to stimulate a first portion of a quadriceps muscle and the second electrode 234 can be actuated to stimulate a second portion of the quadriceps muscle as illustrated in FIG. 21.

With the orthosis device 220 disposed at a desired location on the patient's thigh (e.g., to stimulate the hamstring muscle or the quadriceps muscle), and the gait sensor 204 disposed on the patient's shoe with the pressure sensor 260 placed beneath the insole of the shoe, the control unit 206 can be activated to begin the electrical stimulation treatment. In use, the gait sensor 204 can detect when the patient's foot is in the air and when it is on the ground as the patient moves (e.g., walks, etc.). The transmitter 262 can communicate wirelessly with the stimulator unit 202 to signal the stimulation unit 202 to activate the electrodes 232 and 234 to provide electrical stimulation of the muscle. For example, when the patient's heel leaves the ground, a signal can be sent to the stimulator unit 202 to turn stimulation on, and when the patient's heel contacts the ground, a signal can be sent to the stimulator unit 202 to turn stimulation off. The stimulation can cause the foot and knee to move accordingly.

The orthosis device 220 can also be used when the patient is not walking. For example, the orthosis device 220 can be used in a training mode without the gait sensor 204. The training mode can be designed, for example, to facilitate muscle re-education, prevent or retard disuse atrophy of the lower leg and thigh muscles, maintain or improve range of motion of the ankle and knee joints and/or improve blood circulation.

Figure 23:
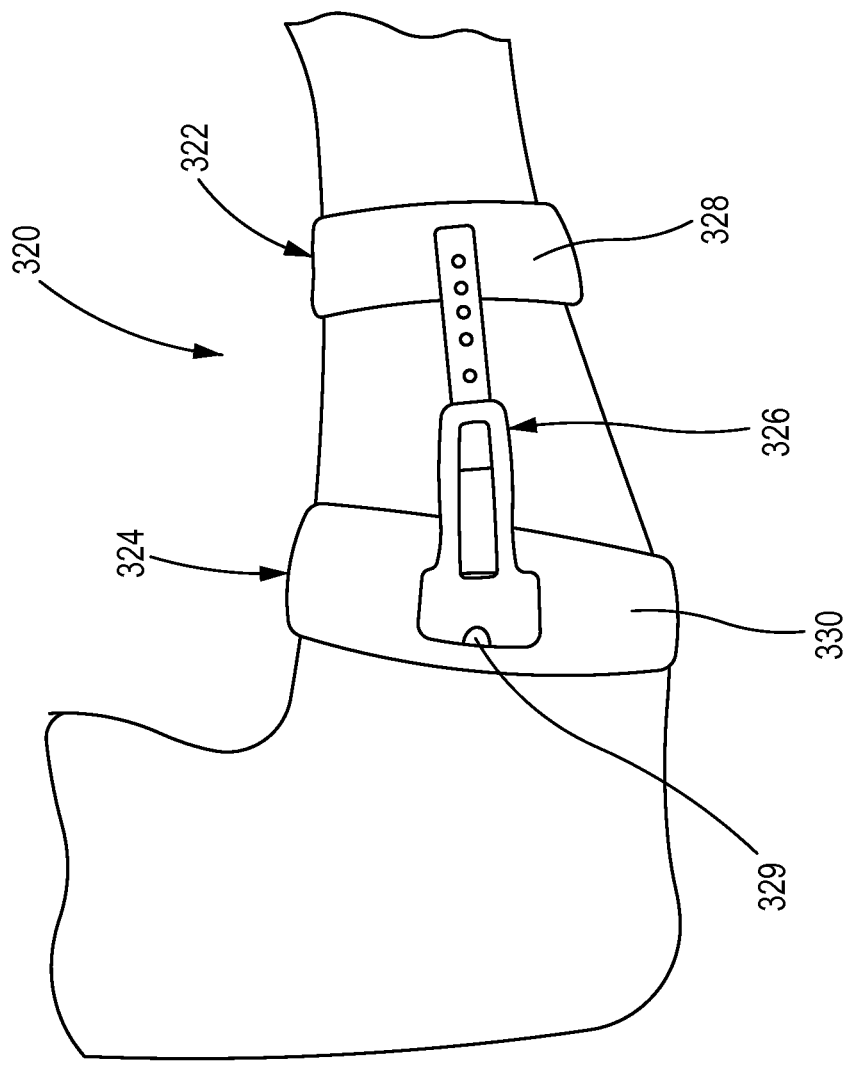
FIG. 23 is a side view of a portion of a patient illustrating an orthosis device according to an embodiment disposed on a forearm.

An orthosis device as described herein can also be used to stimulate various portions of an arm of a patient. FIG. 23 illustrates an orthosis device 320 shown coupled to a portion of an arm of a patient. The orthosis device 320 includes a first orthosis member 322, a second orthosis member 324, a connector 326 and a stimulator unit (not shown). As described above for orthosis devices 120 and 220, the orthosis device 320 can be used to provide electrical stimulation to a portion of a limb of a patient, such as for example, an arm or a leg of the patient. For example, as shown in FIG. 23, the orthosis device 320 can be disposed on a first portion of an arm or leg of the patient and the second orthosis member 324 can be disposed on a second portion of the arm or leg.

As described above for previous embodiments, the connector 326 can be adjusted to change a distance between the first orthosis member 322 and the second orthosis member 324. The connector 326 can also limit movement of the first orthosis member 322 relative to the second orthosis member 324 in a direction substantially parallel to a longitudinal axis of the connector 326.

The first orthosis member 322 includes a first panel or cuff 328 and a first strap assembly (not shown), and the second orthosis member 324 includes a second panel or cuff 330 and a second strap assembly 338. A first electrode (not shown) can be removably coupled to an inner surface of the panel 328 and a second electrode (not shown) can be removably coupled to an inner surface of the second panel 330. The first orthosis member 322 and the second orthosis member 324 are each configured to be coupled to a limb of a patient such that the first electrode and the second electrode can each contact the skin of the patient. As with the previous embodiments, the first electrode can be disposed off-set from a center-line defined by the connector 326, or substantially aligned or centered with the center-line of the connector 326.

The first electrode and the second electrode can each be removably coupled to the first panel 328 and the second panel 330, respectively, with any of the coupling methods described above for previous embodiments. The first orthosis member 322 and the second orthosis member 324 can each be configured the same as, or similar to, the orthosis members described above, such as for example, locator markings (e.g., 280) to help locate the electrodes. Similarly, the first strap assembly and the second strap assembly can each be configured the same as, or similar to, the strap assemblies 236 and 238 described above. The orthosis device 320 can also include a visual locator 329 disposed on the connector 326, as shown in FIG. 23, which can be used to help position the orthosis device 320 on a limb of a patient as described above.

The second orthosis member 324 can includes a cradle (not shown) configured to couple a stimulator unit (not shown), such as stimulator unit 202, thereto. The stimulator unit can be removably coupled to the cradle as described above for previous embodiments. The stimulator unit can include any of the features and functions as described above for stimulators 102 and 202. The stimulator unit can be used to generate and send a signal to the first electrode and the second electrode to stimulate a portion of the patient's body. A control unit (not shown), such as control unit 206 described above, can also be used with orthosis device 320, to control operation of the orthosis device 320. The control unit can include any of the features and functions as described above for control unit 206. For example, the control unit can be configured to communicate wirelessly with the stimulator.

In one example use of the orthosis device 320, the first orthosis member 322 can be disposed about a first portion of an arm such that the first electrode is in contact with the first portion of the arm, and the second orthosis member 324 can be disposed about a second portion of the arm such that the second electrode is in contact with the second portion of the arm. In some embodiments, the orthosis device 320 can be disposed on an arm of a patient such that both the first orthosis member 322 and the second orthosis member 324 are disposed between a first joint and a second joint of the arm.

In some embodiments, the orthosis device 320 can be disposed on an arm of a patient such that the first orthosis member 322 is disposed about a first forearm portion adjacent a wrist and the second orthosis member 324 is disposed about a second forearm portion between the first forearm portion and an elbow of the patient. In some such embodiments, supination and pronation of the forearm can remain uninhibited when the orthosis device 320 is disposed thereon. In some embodiments, the orthosis device 320 can be disposed on an arm of a patient such that flexion and extension of the wrist is uninhibited when disposed about a forearm of the arm. In some embodiments, the orthosis device 320 can be disposed on an arm of a patient such that neither the first orthosis member 322 or the second orthosis member 324 extend adjacent a palm of the patient.

In some embodiments, the first orthosis member 322 can be disposed about a first forearm portion of the arm such that at least a portion of the first electrode is configured to stimulate a muscle, such as, for example, a flexor muscle (e.g., a flexor pollicis longus muscle and/or a flexor digitorum superficialis muscle) and/or an extensor pollicis brevis muscle, and the second orthosis member 324 can be disposed about a second forearm portion of the arm such that at least a portion of the second electrode is configured to stimulate a muscle, such as, for example, an extensor muscle (e.g., an extensor digitorum muscle).

CONCLUSION

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein. Further, although some embodiments of an orthosis device described herein include a single electrode disposed on each of the panels of the orthosis device, it should be understood that in other embodiments any number of electrodes can be included on either panel of an orthosis device.

In addition, the devices and methods described herein can be used for a variety of different types of functional electrical stimulation treatments in a variety of different locations on a patient's body. For example, any of the embodiments of an orthosis device as described herein can be configured for use on a portion of a leg and/or an arm of a patient.

What is claimed is:

1. An apparatus, comprising:
   a first orthosis member including a first electrode, the first orthosis member configured to be disposed about a first portion of a limb of a user of the apparatus such that the first electrode is in contact with the first portion of the limb;
   a second orthosis member including a second electrode, the second orthosis member configured to be disposed about a second portion of the limb such that the second electrode is in contact with the second portion of the limb;
   a connector configured to couple the second orthosis member to the first orthosis member, the connector having a selectively adjustable length and including a first connector member coupled to the first orthosis member and a second connector member coupled to the second orthosis member such that a longitudinal distance between the first orthosis member and the second orthosis member can be adjustably changed; and
   a visual locator in the form of a mark disposed on the apparatus in alignment with a longitudinal centerline of the first connector member and a longitudinal centerline of the second connector member such that the visual locator can be used to align the apparatus on the limb of the user.

2. The apparatus of claim 1, wherein the connector is configured to limit movement of the second orthosis member relative to the first orthosis member in a direction substantially parallel to the longitudinal centerline of the connector.

3. The apparatus of claim 1, wherein the first orthosis member is configured to be disposed about a first portion of a thigh of the user such that the first electrode is in contact with the first portion of the thigh,
   the second orthosis member is configured to be disposed about a second portion of the thigh such that the second electrode is in contact with the second portion of the thigh,
   the first portion of the thigh being at a first distance from a knee of the user, the second portion of the thigh being at a second distance from the knee, the second distance being greater than the first distance.

4. The apparatus of claim 1, wherein the first orthosis member is configured to be disposed about a first portion of a thigh of the user such that at least a portion of the first electrode is configured to stimulate a portion of a hamstring muscle,
   the second orthosis member is configured to be disposed about a second portion of the thigh such that at least a portion of the second electrode is configured to stimulate a second portion of the hamstring muscle.

5. The apparatus of claim 1, wherein the first orthosis member is configured to be disposed about a first portion of a thigh of the user such that at least a portion of the first electrode is configured to stimulate a portion of a quadriceps muscle group, the second orthosis member is configured to be disposed about a second portion of the thigh such that at least a portion of the second electrode is configured to stimulate a second portion of the quadriceps muscle group.

6. The apparatus of claim 1, wherein the first orthosis member is configured to be disposed about a first portion of an arm of the user such that the first electrode is in contact with the first portion of the arm, the second orthosis member is configured to be disposed about a second portion of the arm such that the second electrode is in contact with the second portion of the arm.

7. The apparatus of claim 6, wherein the first portion of the arm is between a first joint and a second joint, and the second portion of the arm is between the first joint and the second joint.

8. The apparatus of claim 6, wherein the first portion of the arm includes a first forearm portion adjacent a wrist, the second portion of the arm includes a second forearm portion between the first forearm portion and an elbow, and supination and pronation of a forearm of the arm is uninhibited when the first orthosis member is disposed about the first forearm portion, the second orthosis member is disposed about the second forearm portion and the second orthosis member is coupled to the first orthosis member.

9. The apparatus of claim 6, wherein the first portion of the arm includes a first forearm portion adjacent a wrist; and the first orthosis member is configured to be disposed at a predetermined location about the first forearm portion such that the first orthosis member does not extend adjacent a palm.

10. The apparatus of claim 6, wherein the first portion of the arm includes a first forearm portion adjacent a wrist, and flexion and extension of the wrist is uninhibited when the first orthosis member is disposed about the first forearm portion.

11. The apparatus of claim 1, wherein the first orthosis member is configured to be disposed about a first forearm portion of an arm such that at least a portion of the first electrode is configured to stimulate at least one of a flexor muscle, and the second orthosis member is configured to be disposed about a second forearm portion of the arm such that at least a portion of the second electrode is configured to stimulate an extensor muscle.

12. The apparatus of claim 1, wherein the connector includes a first connector member coupled to the first orthosis member and a second connector member coupled to the second orthosis member, the first connector member being couplable to the second connector member such that the connector has a preselected length between the first orthosis member and the second orthosis member.

13. The apparatus of claim 1, wherein the apparatus has a first configuration in which the first orthosis member is configured to be disposed about the limb such that the first electrode is in contact with the first portion of the limb, and a second configuration in which the first orthosis member is configured to be disposed about the limb such that the first electrode is in contact with a third portion of the limb.

14. The apparatus of claim 1, wherein the apparatus has a first configuration in which the second orthosis member is configured to be disposed about the limb such that the second electrode is in contact with the second portion of the limb, and a second configuration in which the second orthosis member is configured to be disposed about the limb such that the second electrode is in contact with a fourth portion of the limb.

15. An apparatus, comprising:
an orthosis including
a first cuff member,
a second cuff member, the first cuff member configured to be coupled to the second cuff member at a preselected distance from the first cuff member, the first cuff member configured to have a first electrode coupled thereto, the second cuff member configured to have a second electrode coupled thereto;
a connector configured to adjustably couple the second cuff member to the first cuff member, the connector having a selectively adjustable length; and
a visual locator disposed at least partially on one of the first cuff member and the second cuff member and at least partially on the connector and in alignment with a longitudinal centerline of the connector,
the orthosis configured to be disposed in a first position on a limb of a user such that the visual locator is positioned at a first location on an outer portion of the limb, the first cuff member is disposed about the limb such that the first electrode is in contact with a first portion of the limb, and the second cuff member is disposed about the limb such that the second electrode is in contact with a second portion of the limb,
the orthosis configured to be disposed in a second position on the limb different than the first position such that the visual locator is positioned at a second location on the outer portion of the limb different than the first location, the first cuff member is disposed about the limb such that the first electrode is in contact with a third portion of the limb, and the second cuff member is disposed about the limb such that the second electrode is in contact with a fourth portion of the limb.

16. The apparatus of claim 15, wherein
the connector is configured to limit movement of the second cuff member relative to the first cuff member along a longitudinal axis of the limb.

17. The apparatus of claim 15, wherein
the connector is configured to limit movement of the second cuff member relative to the first cuff member in a direction substantially parallel to a longitudinal axis of the connector.

18. The apparatus of claim 15, further comprising:
the second electrode,
the connector including an electrical conductor configured to be operatively coupled to the second electrode and to an electronic interface of the first cuff member.

19. The apparatus of claim 15, wherein the connector includes a first connector member coupled to the first cuff member and a second connector member coupled to the second cuff member, the first connector member being couplable to the second connector member such that the connector has a preselected length between the first cuff member and the second cuff member.

20. The apparatus of claim 15, wherein when the orthosis is in the first position, the first electrode is configured to stimulate a first portion of a hamstring muscle, and the second electrode is configured to stimulate a second portion of the hamstring muscle.

21. The apparatus of claim 15, wherein when the orthosis is in the second position, the first electrode is configured to stimulate a first portion of a quadriceps muscle group, and the second electrode is configured to stimulate a second portion of the quadriceps muscle group.

22. An apparatus, comprising:

a first orthosis member including a first electrode, the first orthosis member configured to be disposed about a first portion of a thigh of a user of the apparatus such that the first electrode is in contact with the first portion of the thigh;

a second orthosis member including a second electrode, the second orthosis member configured to be disposed about a second portion of the thigh of the user such that the second electrode is in contact with the second portion of the thigh, the first portion of the thigh being at a first distance from a knee of the user, the second portion of the thigh being at a second distance from the knee of the user, the second distance being greater than the first distance;

a connector configured to couple the second orthosis member to the first orthosis member, the connector includes a first connector member coupled to the first orthosis member and a second connector member coupled to the second orthosis member, the first connector member being couplable to the second connector member such that the connector has a preselected length between the first orthosis member and the second orthosis member; and a visual locator in the form of a mark and disposed at least partially on one of the first connector member and the second connector member and in alignment with a longitudinal centerline of the first connector member and a longitudinal centerline of the second connector member.

23. The apparatus of claim 22, wherein the connector is configured to limit movement of the second orthosis member relative to the first orthosis member along a longitudinal axis of the thigh.

24. The apparatus of claim 22, wherein the connector is configured to limit movement of the second orthosis member relative to the first orthosis member in a direction substantially parallel to a longitudinal axis of the connector.

25. The apparatus of claim 22, wherein the first orthosis member is configured to be disposed about the first portion of the thigh such that at least a portion of the first electrode is configured to stimulate a portion of a hamstring muscle; and the second orthosis member is configured to be disposed about the second portion of the thigh such that at least a portion of the second electrode is configured to stimulate a second portion of the hamstring muscle.

26. The apparatus of claim 22, wherein the first orthosis member is configured to be disposed about the first portion of the thigh such that at least a portion of the first electrode is configured to stimulate a portion of a quadriceps muscle group; and the second orthosis member is configured to be disposed about the second portion of the thigh such that at least a portion of the second electrode is configured to stimulate a second portion of the quadriceps muscle group.

27. The apparatus of claim 15, wherein the connector includes a first connector member coupled to the first cuff member and a second connector member coupled to the second cuff member, the visual locator being disposed at least partially on one of the first connector member and the second connector member and in alignment with a longitudinal centerline of the first connector member and a longitudinal centerline of the second connector member.

* * * * *